US012138610B2

(12) United States Patent
Jerri et al.

(10) Patent No.: US 12,138,610 B2
(45) Date of Patent: Nov. 12, 2024

(54) PROCESS FOR PREPARING MINERALIZED MICROCAPSULES

(71) Applicant: FIRMENICH SA, Satigny (CH)

(72) Inventors: Huda Jerri, Plainsboro, NJ (US); Nicholas Impellizzeri, Plainsboro, NJ (US)

(73) Assignee: FIRMENICH SA, Satigny (CH)

( * ) Notice: Subject to any disclaimer, the term of this patent is extended or adjusted under 35 U.S.C. 154(b) by 814 days.

(21) Appl. No.: 16/981,314

(22) PCT Filed: Jun. 19, 2019

(86) PCT No.: PCT/EP2019/066216
§ 371 (c)(1),
(2) Date: Sep. 16, 2020

(87) PCT Pub. No.: WO2019/243427
PCT Pub. Date: Dec. 26, 2019

(65) Prior Publication Data
US 2021/0106965 A1    Apr. 15, 2021

Related U.S. Application Data

(60) Provisional application No. 62/687,878, filed on Jun. 21, 2018.

(30) Foreign Application Priority Data

Jul. 18, 2018 (EP) .................................. 18184288

(51) Int. Cl.
*B01J 13/16* (2006.01)
*A61K 8/11* (2006.01)
(Continued)

(52) U.S. Cl.
CPC .................. *B01J 13/16* (2013.01); *A61K 8/11* (2013.01); *A61Q 5/02* (2013.01); *A61Q 5/12* (2013.01);
(Continued)

(58) Field of Classification Search
CPC ............. B01J 13/16; B01J 13/22; A61K 8/11; A61K 2800/10; A61K 2800/412;
(Continued)

(56) References Cited

U.S. PATENT DOCUMENTS 4,489,017 A    12/1984   Alberts et al.
2010/0272764 A1   10/2010   Latta et al.

FOREIGN PATENT DOCUMENTS

CN    102939151 A    2/2013
CN    108003299 A    5/2018
(Continued)

OTHER PUBLICATIONS

International Search Report and Written Opinion for corresponding PCT/EP2019/066216 mailed Aug. 14, 2019, 13 pages.

*Primary Examiner* — Frances Tischler
(74) *Attorney, Agent, or Firm* — Armstrong Teasdale LLP

(57) ABSTRACT

Described herein is a process for preparing a mineralized core-shell microcapsule slurry, where the mineralized microcapsules have a mineral layer. The process is notably characterized by the fact that a low amount of polyisocyanate is required during the process.
Also described herein is a mineralized core-shell microcapsule slurry obtainable by said process.
Also described herein are perfuming compositions and consumer products comprising said microcapsules, in particular perfumed consumer products in the form of home care or personal care products.

18 Claims, 6 Drawing Sheets

(51) Int. Cl.
*A61Q 5/02* (2006.01)
*A61Q 5/12* (2006.01)
*A61Q 19/10* (2006.01)
*B01J 13/22* (2006.01)
*C11D 3/50* (2006.01)

(52) U.S. Cl.
CPC .............. *A61Q 19/10* (2013.01); *B01J 13/22* (2013.01); *C11D 3/505* (2013.01); *A61K 2800/10* (2013.01); *A61K 2800/412* (2013.01); *A61K 2800/624* (2013.01)

(58) Field of Classification Search
CPC ...... A61K 2800/624; A61Q 5/02; A61Q 5/12; A61Q 19/10; C11D 3/505; H04W 4/24; H04W 88/04
See application file for complete search history.

(56) References Cited

FOREIGN PATENT DOCUMENTS

| | | |
|---|---|---|
| JP | S5621640 A | 2/1981 |
| WO | 2010003762 A1 | 1/2010 |
| WO | 2017058875 A1 | 4/2017 |
| WO | 2018054719 A1 | 3/2018 |
| WO | 2018115330 A1 | 6/2018 |

PROCESS FOR PREPARING MINERALIZED MICROCAPSULES

CROSS-REFERENCE TO RELATED APPLICATIONS

This application is a U.S. National Phase Application of PCT/EP2019/066216, filed Jun. 19, 2019, which claims the benefit of priority to U.S. Provisional Patent Application No.

TECHNICAL FIELD

The present invention relates to a process for preparing a mineralized core-shell microcapsule slurry, wherein the mineralized microcapsules have a mineral layer. The process is notably characterized by the fact that a low amount of polyisocyanate is required during the process.

A mineralized core-shell microcapsule slurry obtainable by said process is also an object of the invention.

Perfuming compositions and consumer products comprising said microcapsules, in particular perfumed consumer products in the form of home care or personal care products, are also part of the invention.

BACKGROUND OF THE INVENTION

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

In order to be successfully used in consumer products, perfume delivery systems must meet a certain number of criteria. The first requirement concerns stability in aggressive medium. In fact delivery systems may suffer from stability problems, in particular when incorporated into surfactant-based products such as detergents, wherein said systems tend to degrade and lose efficiency in the perfume-retention ability. It is also difficult to have a good stability and a good dispersion of the capsules altogether. The dispersion factor is very important because the aggregation of capsules increases the tendency of the capsule-containing product to phase separate, which represents a real disadvantage. On the other hand, perfume delivery systems must also perform during the actual use of the end-product by the consumer, in particular in terms of odor performance, as the perfume needs to be released when required. Another issue faced for example by the perfumery industry is to provide delivery systems that are well deposited on the substrate for the treatment of which the end product is intended to be used, such as textile, skin, hair or other surfaces, so as to possibly remain on the substrate even after a rinsing step. To address this specific problem, the use of cationic capsules has been described in the prior art. Cationic capsules are also known to be better dispersed in several applications.

For example, WO 01/41915 discloses a process for the preparation of capsules carrying cationic charges. Such a process is allegedly applicable to a large variety of microcapsules, in particular polyurethane-polyurea microcapsules are mentioned. After their formation, the capsules are placed in a medium which is favourable for the treatment with cationic polymers. The treatment with cationic polymers is carried out after purification of the basic capsule slurry, in order to eliminate anionic or neutral polymers which were not incorporated in the capsule wall during formation thereof, and other free electrically charged compounds involved in the encapsulation process. In particular, the capsules are diluted, isolated and then re-suspended in water, or even washed to further eliminate anionic compounds. After the purification step, the capsules are agitated vigorously and the cationic polymers are added. Partially quaternized copolymers of polyvinylpyrrolidones are cited to this purpose, among many other suitable polymers. The described process comprises several steps following the capsule formation, said process being therefore time consuming and not economically profitable.

US 2006/0216509 also discloses a process to render polyurea capsules positively-charged. This process involves the addition, during the wall formation, of polyamines, the capsules thus bearing latent charges, depending on the pH of the medium. Once formed, the capsules are subsequently cationized by acid action or alkylation to bear permanent positive charges. The cationic compounds therefore react with the capsule wall, chemically changing the latter.

WO2009/153695 discloses a simplified process for the preparation of polyurea microcapsules bearing permanent positive charges based on the use of a specific stabilizer and which present good deposition on a substrate.

Therefore, there is still a need to use new delivery systems, while not compromising on the performance of the microcapsules, in particular in terms of deposition and stability in a consumer product, as well as in delivering a good performance in terms of active ingredient delivery.

The invention solves this problem as it provides new microcapsules and a process using a limited amount of polyisocyanate for preparing microcapsules that show improvement in terms of deposition properties compared to what was known heretofore such as cationic delivery systems.

SUMMARY OF THE INVENTION

The present invention provides a process for preparing microcapsules with boosted deposition properties. In particular, the specific growth of a mineral layer onto the shell of the microcapsule is unexpectedly tremendously improving the percentage of deposition of microcapsules on a substrate. Furthermore, even if a limited amount of polyisocyanate is used during the process, said microcapsules show satisfactory stability in consumer bases.

A first object of the invention is therefore a process for preparing a mineralized core-shell microcapsule slurry comprising the steps of:
  (i) dissolving at least one polyisocyanate having at least two isocyanate groups in an oil comprising a hydrophobic material, preferably a perfume oil, to form an oil phase; (ii) preparing an aqueous solution of a charged emulsifier to form a water phase; (iii) adding the oil phase to the water phase to form an oil-in-water emulsion;
  (iv) applying conditions suitable to induce interfacial polymerization to form core-shell microcapsules in the form of a slurry;
  (v) adsorption of at least one mineral precursor on the microcapsule shell;
  (vi) applying conditions suitable to induce growth of a mineral layer on the microcapsule shell,
    characterized in that the polyisocyanate is added in an amount less than 1% by weight based on the total weight of the slurry of step (iv).

A second object of the invention is a mineralized core-shell microcapsule slurry obtainable by the process as defined above.

A third object of the invention is a perfuming composition comprising the microcapsules as defined above, wherein the oil-based core comprises a perfume.

A fourth object of the invention is a consumer product comprising the microcapsules or a perfuming composition as defined above.

A fifth object of the invention is a method for improving deposition of microcapsules on a surface, which comprises treating said surface with a perfuming composition or a consumer product as defined above.

DETAILED DESCRIPTION OF THE INVENTION

Figure 1:
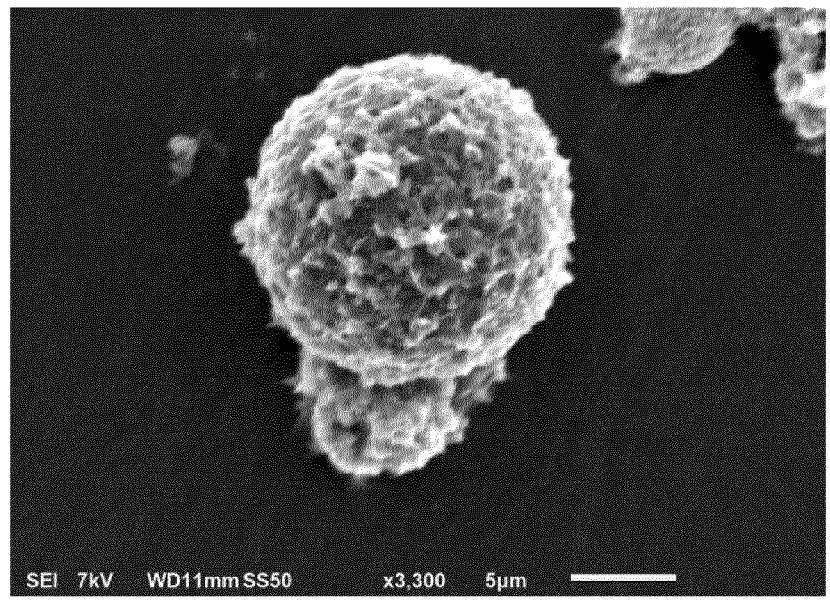
FIG. 1 represents scanning electron micrographs of mineralized microcapsules according to the invention (Capsules A).
Figure 2:
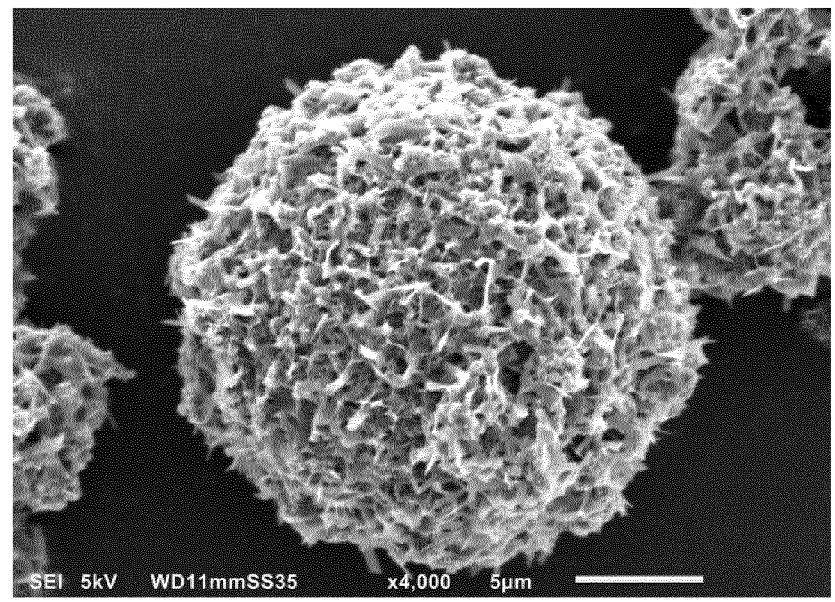
FIG. 2 represents scanning electron micrographs of mineralized microcapsules according to the invention (Capsules B).
Figure 3:
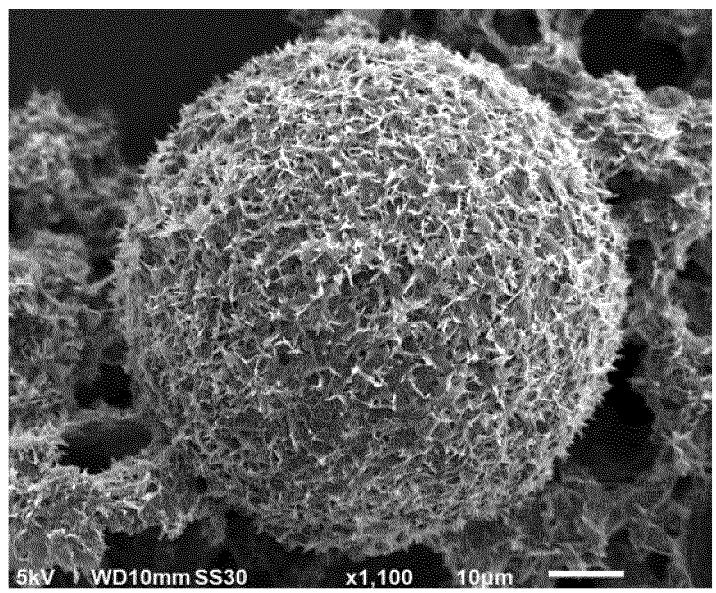
FIG. 3 represents scanning electron micrographs of mineralized microcapsules according to the invention (Capsules C).
Figure 4:
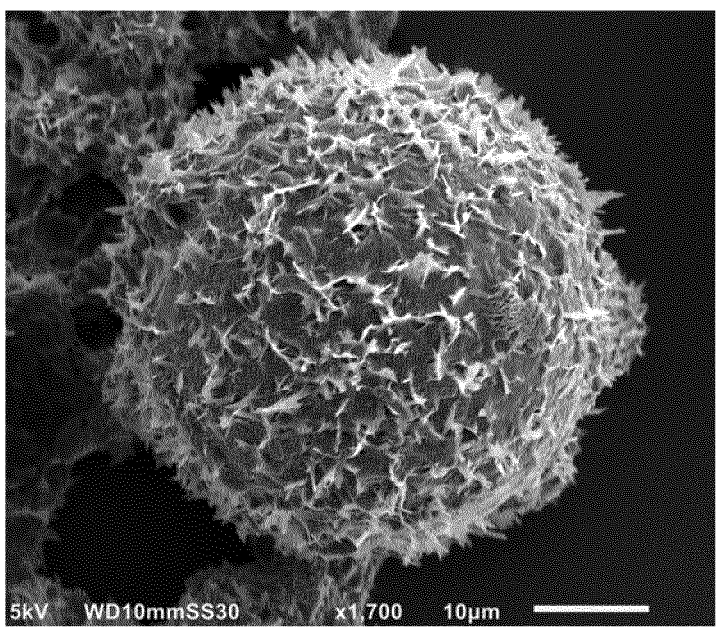
FIG. 4 represents scanning electron micrographs of mineralized microcapsules according to the invention (Capsules D).

Unless stated otherwise, percentages (%) are meant to designate a percentage by weight of a composition.

Definitions

A "core-shell microcapsule", or the similar, in the present invention is meant to designate a capsule that has a particle size distribution in the micron range (e.g. a mean diameter (d(v, 0.5)) comprised between about 1 and 3000 μm) and comprises an external solid oligomer-based shell or a polymeric shell and an internal continuous phase enclosed by the external shell. For avoidance of doubts coacervates are considered as core-shell microcapsules in the present invention.

By "mineralized core-shell microcapsule", it should be understood a microcapsule having a mineralized surface induced by growth of inorganic solid crystalline or amorphous material.

By "charged emulsifier" it should be understood a compound having emulsifying properties and that is negatively charged and/or positively charged. The charged emulsifier can be a charged biopolymer.

By "charged biopolymer" it should be understood a biopolymer that is negatively charged (anionic biopolymer), and/or positively charged (cationic or protonated biopolymer), and/or zwitterionic. As non-limiting examples, one may cite gum acacia, pectin, sericin, sodium caseinate and amphiphilic proteins such as soy, pea, milk, bovine serum albumin, gelatin as anionic biopolymers.

By "biopolymers" it is meant biomacromolecules produced by living organisms. Biopolymers are characterized by molecular weight distributions ranging from 1,000 (1 thousand) to 1,000,000,000 (1 billion) Daltons. These macromolecules may be carbohydrates (sugar based) or proteins (amino-acid based) or a combination of both (gums) and can be linear or branched. The biopolymers according to the invention may be further chemically modified.

According to an embodiment, biopolymers are amphiphilic or anionic namely negatively charged in water at a pH greater than 9.

In the context of the invention, a "mineral layer" is composed of a stable inorganic crystalline or amorphous phase that grows normal to the terminating charged surface of the shell to yield a textured mineral surface.

By "mineral precursor", it should be understood a mineral precursor required for growth of the desired mineral phase. The mineral precursor is preferably a mineral water-soluble salt containing at least one part of the necessary ions for growth of the desired solid mineral phase.

The terminology of "incubating" is used in the context of the present invention to describe the act of submerging the microcapsules in the precursor solution and allowing it time to interact with the microcapsules.

By "polyurea-based" wall or shell, it is meant that the polymer comprises urea linkages produced by either an amino-functional crosslinker or hydrolysis of isocyanate groups to produce amino groups capable of further reacting with isocyanate groups during interfacial polymerization.

By "polyurethane-based" wall or shell, it is meant that the polymer comprises urethane linkages produced by reaction of a polyol with the isocyanate groups during interfacial polymerization.

For the sake of clarity, by the expression "dispersion" in the present invention it is meant a system in which particles are dispersed in a continuous phase of a different composition and it specifically includes a suspension or an emulsion.

"Hydrophobic material" according to the invention can be "inert" material like solvents or active ingredients.
According to an embodiment, the hydrophobic material is a hydrophobic active ingredient.

By "active ingredient", it is meant any material—single ingredient or a mixture of ingredients—which forms a two-phase dispersion when mixed with water.

Hydrophobic active ingredients are preferably chosen from the group consisting of flavor, flavor ingredients, perfume, perfume ingredients, nutraceuticals, cosmetics, insect control agents, biocide actives and mixtures thereof.

The nature and type of the insect control agents that can be present in the hydrophobic internal phase do not warrant a more detailed description here, which in any case would not be exhaustive, the skilled person being able to select them on the basis of its general knowledge and according to the intended use or application.

Examples of such insect control agents are birch, DEET (N,N-diethyl-m-toluamide), essential oil of the lemon eucalyptus (*Corymbia citriodora*) and its active compound p-menthane-3,8-diol(PMD), icaridin (hydroxyethyl isobutyl piperidine carboxylate), Nepelactone, Citronella oil, Neem oil, Bog Myrtle (*Myrica gale*), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, S S220, anthranilate-based insect repellents, and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odor. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodor counteraction, antimicrobial effect, microbial stability, insect control.

The nature and type of the perfuming ingredients present in the hydrophobic internal phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Preferred perfuming ingredients are those having a high steric hindrance and in particular those from one of the following groups:

Group 1: perfuming ingredients comprising a cyclohexane, cyclohexene, cyclohexanone or cyclohexenone ring substituted with at least one linear or branched $C_1$ to $C_4$ alkyl or alkenyl substituent;

Group 2: perfuming ingredients comprising a cyclopentane, cyclopentene, cyclopentanone or cyclopentenone ring substituted with at least one linear or branched $C_4$ to $C_8$ alkyl or alkenyl substituent;

Group 3: perfuming ingredients comprising a phenyl ring or perfuming ingredients comprising a cyclohexane, cyclohexene, cyclohexanone or cyclohexenone ring substituted with at least one linear or branched $C_5$ to $C_8$ alkyl or alkenyl substituent or with at least one phenyl substituent and optionally one or more linear or branched $C_1$ to $C_3$ alkyl or alkenyl substituents;

Group 4: perfuming ingredients comprising at least two fused or linked $C_5$ and/or $C_6$ rings;

Group 5: perfuming ingredients comprising a camphor-like ring structure;

Group 6: perfuming ingredients comprising at least one C7 to C20 ring structure;

Group 7: perfuming ingredients having a log P value above 3.5 and comprising at least one tert-butyl or at least one trichloromethyl substitutent;

Examples of ingredients from each of these groups are:

Group 1: 2,4-dimethyl-3-cyclohexene-1-carbaldehyde (origin: Firmenich SA, Geneva, Switzerland), isocyclocitral, menthone, isomenthone, Romascone® (methyl 2,2-dimethyl-6-methylene-1-cyclohexanecarboxylate, origin: Firmenich SA, Geneva, Switzerland), nerone, terpineol, dihydroterpineol, terpenyl acetate, dihydroterpenyl acetate, dipentene, eucalyptol, hexylate, rose oxide, Perycorolle® ((S)-1,8-p-menthadiene-7-ol, origin: Firmenich SA, Geneva, Switzerland), 1-p-menthene-4-ol, (1RS,3RS,4SR)-3-p-mentanyl acetate, (1R,2S,4R)-4,6,6-trimethyl-bicyclo[3,1,1]heptan-2-ol, Doremox® (tetrahydro-4-methyl-2-phenyl-2H-pyran, origin: Firmenich SA, Geneva, Switzerland), cyclohexyl acetate, cyclanol acetate, Fructalate® (1,4-cyclohexane diethyldicarboxylate, origin: Firmenich SA, Geneva, Switzerland), Koumalactone® ((3ARS,6SR, 7ASR)-perhydro-3,6-dimethyl-benzo[B]furan-2-one, origin: Firmenich SA, Geneva, Switzerland), Natactone® ((6R)-perhydro-3,6-dimethyl-benzo[B]furan-2-one, origin: Firmenich SA, Geneva, Switzerland), 2,4, 6-trimethyl-4-phenyl-1,3-dioxane, 2,4,6-trimethyl-3-cyclohexene-1-carbaldehyde;

Group 2: (E)-3-methyl-5-(2,2,3-trimethyl-3-cyclopenten-1-yl)-4-penten-2-ol (origin: Givaudan SA, Vernier, Switzerland), (1'R,E)-2-ethyl-4-(2',2',3'-trimethyl-3'-cyclopenten-1'-yL)-2-buten-1-ol (origin: Firmenich SA, Geneva, Switzerland), Polysantol® ((1'R,E)-3,3-dimethyl-5-(2',2',3'-trimethyl-3'-cyclopenten-1'-yl)-4-penten-2-ol, origin: Firmenich SA, Geneva, Switzerland), fleuramone, Hedione® HC (methyl-cis-3-oxo-2-pentyl-1-® acetate, origin: Firmenich SA, Geneva, Switzerland), Veloutone® (2,2,5-Trimethyl-5-pentyl-1-cyclopentanone, origin: Firmenich SA, Geneva, Switzerland), Nirvanol® (3,3-dimethyl-5-(2,2,3-trimethyl-3-cyclopenten-1-yl)-4-penten-2-ol, origin: Firmenich SA, Geneva, Switzerland), 3-methyl-5-(2,2,3- trimethyl-3-cyclopenten-1-yl)-2-pentanol (origin, Givaudan SA, Vernier, Switzerland);

Group 3: damascones, Neobutenone® (1-(5,5-dimethyl-1-cyclohexen-1-yl)-4-penten-1-one, origin: Firmenich SA, Geneva, Switzerland), nectalactone ((1'R)-2-[2-(4'-methyl-3'-cyclohexen-1'-yl)propyl]cyclopentanone), alpha-ionone, beta-ionone, damascenone, Dynascone® (mixture of 1-(5,5-dimethyl-1-cyclohexen-1-yl)-4-penten-1-one and 1-(3,3-dimethyl-1-cyclohexen-1-yl)-4-penten-1-one, origin: Firmenich SA, Geneva, Switzerland), Dorinone® beta (1-(2,6,6-trimethyl-1-cyclohexen-1-yl)-2-buten-1-one, origin: Firmenich SA, Geneva, Switzerland), Romandolide® ((1S,1'R)-[1-(3',3'-Dimethyl-1'-cyclohexyl)ethoxycarbonyl]methyl propanoate, origin: Firmenich SA, Geneva, Switzerland), 2-tert-butyl-1-cyclohexyl acetate (origin: International Flavors and Fragrances, USA), Limbanol® (1-(2,2,3,6-tetramethyl-cyclohexyl)-3-hexanol, origin: Firmenich SA, Geneva, Switzerland), trans-1-(2,2,6-trimethyl-1-cyclohexyl)-3-hexanol (origin: Firmenich SA, Geneva, Switzerland), (E)-3-methyl-4-(2,6,6-trimethyl-2-cyclohexen-1-yl)-3-buten-2-one, terpenyl isobutyrate, Lorysia® (4-(1,1-dimethylethyl)-1-cyclohexyl acetate, origin: Firmenich SA, Geneva, Switzerland), 8-methoxy-1-p-menthene, Helvetolide® ((1S,1'R)-2-[1-(3',3'-dimethyl-1'-cyclohexyl) ethoxy]-2-methylpropyl propanoate, origin: Firmenich SA, Geneva, Switzerland), para tert-butylcyclohexanone, menthenethiol, 1-methyl-4-(4-methyl-3-pentenyl)-3-cyclohexene-1-carbaldehyde, allyl cyclohexylpropionate, cyclohexyl salicylate, 2-methoxy-4-methylphenyl methyl carbonate, ethyl 2-methoxy-4-methylphenyl carbonate, 4-ethyl-2-methoxyphenyl methyl carbonate;

Group 4: Methyl cedryl ketone (origin: International Flavors and Fragrances, USA), Verdylate, vetyverol, vetyverone, 1-(octahydro-2,3,8,8-tetramethyl-2-naphtalenyl)-1-ethanone (origin: International Flavors and Fragrances, USA), (5RS,9RS,10SR)-2,6,9,10-tetramethyl-1-oxaspiro[4.5]deca-3,6-diene and the (5RS,9SR,10RS) isomer, 6-ethyl-2,10,10-trimethyl-1-oxaspiro[4.5]deca-3,6-diene, 1,2,3,5,6,7-hexahydro-1,1,2,3,3-pentamethyl-4-indenone (origin: International Flavors and Fragrances, USA), Hivernal® (a mixture of 3-(3,3-dimethyl-5-indanyl)propanal and 3-(1,1-dimethyl-5-indanyl)propanal, origin: Firmenich SA, Geneva, Switzerland), Rhubofix® (3',4-dimethyl-tricyclo[6.2.1.0(2,7)]undec-4-ene-9-spiro-2'-oxirane, origin: Firmenich SA, Geneva, Switzerland), 9/10-ethyldiene-3-oxatricyclo[6.2.1.0(2,7)]undecane, Polywood® (perhydro-5,5,8A-trimethyl-2-naphthalenyl acetate, origin: Firmenich SA, Geneva, Switzerland), octalynol, Cetalox® (dodecahydro-3a,6,6,9a-tetramethyl-naphtho[2,1-b]furan, origin: Firmenich SA, Geneva, Switzerland), tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate, (+)-(1S,2S,3S)-2,6,6-trimethyl-bicyclo[3.1.1]heptane-3-spiro-2'-cyclohexen-4'-one;

Group 5: camphor, borneol, isobornyl acetate, 8-isopropyl-6-methyl-bicyclo[2.2.2]oct-5-ene-2-carbaldehyde, camphopinene, cedramber (8-methoxy-2,6,6,8-tetramethyl-tricyclo[5.3.1.0(1,5)]undecane, origin: Firmenich SA, Geneva, Switzerland), cedrene, cedrenol, cedrol, Florex® (mixture of 9-ethylidene-3-oxatricyclo[6.2.1.0(2,7)]undecan-4-one and 10-ethylidene-3-oxatricyclo[6.2.1.0(2,7)]undecan-4-one, origin: Firmenich SA, Geneva, Switzerland), 3-methoxy-7,7-dimethyl-10-methylene-bicyclo[4.3.1]decane (origin: Firmenich SA, Geneva, Switzerland);

Group 6: Cedroxyde® (trimethyl-13-oxabicyclo-[10.1.0]-trideca-4,8-diene, origin: Firmenich SA, Geneva, Switzerland), Ambrettolide LG ((E)-9-hexadecen-16-olide, origin: Firmenich SA, Geneva, Switzerland), Habanolide® (pentadecenolide, origin: Firmenich SA, Geneva, Switzerland), muscenone (3-methyl-(4/5)-cyclopentadecenone, origin: Firmenich SA, Geneva, Switzerland), muscone (origin: Firmenich SA, Geneva, Switzerland), Exaltolide® (pentadecanolide, origin: Firmenich SA, Geneva, Switzerland), Exaltone® (cyclopentadecanone, origin: Firmenich SA, Geneva, Switzerland), (1-ethoxyethoxy)cyclododecane (origin: Firmenich SA, Geneva, Switzerland), Astrotone, 4,8-cyclodecadien-1-one;

Group 7: Lilial® (origin: Givaudan SA, Vernier, Switzerland), rosinol.

Preferably, the perfume comprises at least 30%, preferably at least 50%, more preferably at least 60% of ingredients selected from Groups 1 to 7, as defined above. More preferably said perfume comprises at least 30%, preferably at least 50% of ingredients from Groups 3 to 7, as defined above. Most preferably said perfume comprises at least 30%, preferably at least 50% of ingredients from Groups 3, 4, 6 or 7, as defined above.

According to another preferred embodiment, the perfume comprises at least 30%, preferably at least 50%, more preferably at least 60% of ingredients having a log P above 3, preferably above 3.5 and even more preferably above 3.75.

Preferably, the perfume used in the invention contains less than 10% of its own weight of primary alcohols, less than 15% of its own weight of secondary alcohols and less than 20% of its own weight of tertiary alcohols. Advantageously, the perfume used in the invention does not contain any primary alcohols and contains less than 15% of secondary and tertiary alcohols. According to an embodiment, the oil phase (or the oil-based core) comprises:

25-100 wt % of a perfume oil comprising at least 15 wt % of high impact perfume raw materials having a Log T<−4, and 0-75 wt % of a density balancing material having a density greater than 1.07 g/cm$^3$.

"High impact perfume raw materials" should be understood as perfume raw materials having a Log T<−4. The odor threshold concentration of a chemical compound is determined in part by its shape, polarity, partial charges and molecular mass. For convenience, the threshold concentration is presented as the common logarithm of the threshold concentration, i.e., Log [Threshold] ("Log T").

A "density balancing material" should be understood as a material having a density greater than 1.07 g/cm$^3$ and having preferably low or no odor.

The odor threshold concentration of a perfuming compound is determined by using a gas chromatograph ("GC"). Specifically, the gas chromatograph is calibrated to determine the exact volume of the perfume oil ingredient injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and hence the concentration of the perfuming compound. To determine the threshold concentration, solutions are delivered to the sniff port at the back-calculated concentration. A panelist sniffs the GC effluent and identifies the retention time when odor is noticed. The average across all panelists determines the odor threshold concentration of the perfuming compound. The determination of odor threshold is described in more detail in C. Vuilleumier et al., Multidimensional Visualization of Physical and Perceptual Data Leading to a Creative Approach in Fragrance Development, Perfume & Flavorist, Vol. 33, September, 2008, pages 54-61.

The nature of high impact perfume raw materials having a Log T<−4 and density balancing material having a density greater than 1.07 g/cm³ are described in WO2018115250, the content of which are included by reference.

According to an embodiment, the high impact perfume raw materials having a Log T<−4 are selected from the list in Table A below.

TABLE A high impact perfume raw materials having a Log T < −4
Perfume raw materials (Log T < −4)

(+−)-1-METHOXY-3-HEXANETHIOL
4-(4-HYDROXY-1-PHENYL)-2-BUTANONE
(+−)-2-(4-METHYL-3-CYCLOHEXEN-1-YL)-2-PROPANETHIOL
2-METHOXY-4-(1-PROPENYL)-1-PHENYL ACETATE
PYRAZOBUTYLE
3-PROPYLPHENOL
1-(3-METHYL-1-BENZOFURAN-2-YL)ETHANONE
2-(3-PHENYLPROPYL)PYRIDINE
1-(3,3-DIMETHYL-1-CYCLOHEXEN-1-YL)-4-PENTEN-1-ONE (A) +
1-(5,5-DIMETHYL-1-CYCLOHEXEN-1-YL)-4-PENTEN-1-ONE (B)
1-(5,5-DIMETHYL-1-CYCLOHEXEN-1-YL)-4-PENTEN-1-ONE
(3RS,3ARS,6SR,7ASR)-PERHYDRO-3,6-DIMETHYL-BENZO[B]FURAN-2-ONE (A) + (3SR,3ARS,6SR,7ASR)-PERHYDRO-3,6-DIMETHYL-BENZO[B]FURAN-2-ONE (B)
(+−)-1-(5-ETHYL-5-METHYL-1-CYCLOHEXEN-1-YL)-4-PENTEN-1-ONE
(1'S,3'R)-1-METHYL-2-[(1',2',2'-TRIMETHYLBICYCLO[3.1.0]HEX-3'-YL)METHYL]CYCLOPROPYL}METHANOL
(+−)-3-MERCAPTOHEXYL ACETATE
(2E)-1-(2,6,6-TRIMETHYL-1,3-CYCLOHEXADIEN-1-YL)-2-BUTEN-1-ONE
7-METHYL-2H-1,5-BENZODIOXEPIN-3(4H)-ONE
(2E,6Z)-2,6-NONADIEN-1-OL
(4Z)-4-DODECENAL
(+−)-4-HYDROXY-2,5-DIMETHYL-3(2H)-FURANONE
METHYL 2,4-DIHYDROXY-3,6-DIMETHYLBENZOATE
3-METHYLINDOLE
(+−)-PERHYDRO-4ALPHA,8ABETA-DIMETHYL-4A-NAPHTHALENOL
PATCHOULOL
2-METHOXY-4-(1-PROPENYL)PHENOL
(+−)-5,6-DIHYDRO-4-METHYL-2-PHENYL-2H-PYRAN (A) + TETRAHYDRO-4-METHYLENE-2-PHENYL-2H-PYRAN (B)
4-METHYLENE-2-PHENYLTETRAHYDRO-2H-PYRAN (A) + (+−)-4-METHYL-2-PHENYL-3,6-DIHYDRO-2H-PYRAN (B)
4-HYDROXY-3-METHOXYBENZALDEHYDE
NONYLENIC ALDEHYDE
2-METHOXY-4-PROPYLPHENOL
(2Z)-3-METHYL-5-PHENYL-2-PENTENENITRILE (A) + (2E)-3-METHYL-5-PHENYL-2-PENTENENITRILE (B)
1-(SPIRO[4.5]DEC-6-EN-7-YL)-4-PENTEN-1-ONE (A) + 1-(SPIRO[4.5]DEC-7-EN-7-YL)-4-PENTEN-1-ONE (B)
2-METHOXYNAPHTHALENE
(−)-(3AR,5AS,9AS,9BR)-3A,6,6,9A-TETRAMETHYLDODECAHYDRONAPHTHO[2,1-B]FURAN
5-NONANOLIDE
(3AR,5AS,9AS,9BR)-3A,6,6,9A-TETRAMETHYLDODECAHYDRONAPHTHO[2,1-B]FURAN
7-ISOPROPYL-2H,4H-1,5-BENZODIOXEPIN-3-ONE
COUMARIN
4-METHYLPHENYL ISOBUTYRATE

TABLE A-continued high impact perfume raw materials having a Log T < −4
Perfume raw materials (Log T < −4)

(2E)-1-(2,6,6-TRIMETHYL-1,3-CYCLOHEXADIEN-1-YL)-2-BUTEN-1-ONE
BETA,2,2,3-TETRAMETHYL-DELTA-METHYLENE-3-CYCLOPENTENE-1-BUTANOL
DELTA DAMASCONE ((2E)-1-[(1RS,2SR)-2,6,6-TRIMETHYL-3-CYCLOHEXEN-1-YL]-2-BUTEN-1-ONE)
(+−)-3,6-DIHYDRO-4,6-DIMETHYL-2-PHENYL-2H-PYRAN
ANISALDEHYDE
PARACRESOL
3-ETHOXY-4-HYDROXYBENZALDEHYDE
METHYL 2-AMINOBENZOATE
ETHYL METHYLPHENYLGLYCIDATE
OCTALACTONE G
ETHYL 3-PHENYL-2-PROPENOATE
(−)-(2E)-2-ETHYL-4-[(1R)-2,2,3-TRIMETHYL-3-CYCLOPENTEN-1-YL]-2-BUTEN-1-OL
PARACRESYL ACETATE
DODECALACTONE
TRICYCLONE
(+)-(3R,5Z)-3-METHYL-5-CYCLOPENTADECEN-1-ONE
UNDECALACTONE
(1R,4R)-8-MERCAPTO-3-P-MENTHANONE
(3S,3AS,6R,7AR)-3,6-DIMETHYLHEXAHYDRO-1-BENZOFURAN-2(3H)-ONE
BETA IONONE
(+−)-6-PENTYLTETRAHYDRO-2H-PYRAN-2-ONE
(3E,5Z)-1,3,5-UNDECATRIENE
10-UNDECENAL (A) + (9E)-9-UNDECENAL (B) + (9Z)-9-UNDECENAL (C)
(Z)-4-DECENAL
(+−)-ETHYL 2-METHYLPENTANOATE
1,2-DIALLYLDISULFANE
(2Z)-2-TRIDECENENITRILE (A) + (3Z)-3-TRIDECENENITRILE (B) + (3E)-3-TRIDECENENITRILE (C) + (2E)-2-TRIDECENENITRILE (D)
(+−)-2-ETHYL-4,4-DIMETHYL-1,3-OXATHIANE
(+)-(3R,5Z)-3-METHYL-5-CYCLOPENTADECEN-1-ONE
3-(4-TERT-BUTYLPHENYL)PROPANAL
ALLYL (CYCLOHEXYLOXY)ACETATE
METHYLNAPHTHYLKETONE
(+−)-(4E)-3-METHYL-4-CYCLOPENTADECEN-1-ONE (A) + (+−)-(5E)-3-METHYL-5-CYCLOPENTADECEN-1-ONE (B) + (+−)-(5Z)-3-METHYL-5-CYCLOPENTADECEN-1-ONE (C)
CYCLOPROPYLMETHYL (3Z)-3-HEXENOATE (A) + CYCLOPROPYLMETHYL (3E)-3-HEXENOATE (B)
(4E)-4-METHYL-5-(4-METHYLPHENYL)-4-PENTENAL
(+−)-1-(5-PROPYL-1,3-BENZODIOXOL-2-YL)ETHANONE
4-METHYL-2-PENTYLPYRIDINE
(+−)-(E)-3-METHYL-4-(2,6,6-TRIMETHYL-2-CYCLOHEXEN-1-YL)-3-BUTEN-2-ONE
(3ARS,5ASR,9ASR,9BRS)-3A,6,6,9A-TETRAMETHYLDODECAHYDRONAPHTHO[2,1-B]FURAN
(2S,5R)-5-METHYL-2-(2-PROPANYL)CYCLOHEXANONE OXIME
6-HEXYLTETRAHYDRO-2H-PYRAN-2-ONE
(+−)-3-(3-ISOPROPYL-1-PHENYL)BUTANAL
METHYL 2-((1RS,2RS)-3-OXO-2-PENTYLCYCLOPENTYL)ACETATE (A) + METHYL 2-((1RS,2SR)-3-OXO-2-PENTYLCYCLOPENTYL)ACETATE (B)
1-(2,6,6-TRIMETHYL-1-CYCLOHEX-2-ENYL)PENT-1-EN-3-ONE
INDOL
7-PROPYL-2H,4H-1,5-BENZODIOXEPIN-3-ONE
ETHYL PRALINE
(4-METHYLPHENOXY)ACETALDEHYDE
ETHYL TRICYCLO[5.2.1.0.(2,6)]DECANE-2-CARBOXYLATE
(+)-(1'S,2S,E)-3,3-DIMETHYL-5-(2',2',3'-TRIMETHYL-3'-CYCLOPENTEN-1'-YL)-4-PENTEN-2-OL
(2R,4E)-3,3-DIMETHYL-5-[(1R)-2,2,3-TRIMETHYL-3-CYCLOPENTEN-1-YL]-4-PENTEN-2-OL (A) + (2S,4E)-3,3-DIMETHYL-5-[(1R)-2,2,3-TRIMETHYL-3-CYCLOPENTEN-1-YL]-4-PENTEN-2-OL (B)
8-ISOPROPYL-6-METHYL-BICYCLO[2.2.2]OCT-5-ENE-2-CARBALDEHYDE
METHYLNONYLACETALDEHYDE
4-FORMYL-2-METHOXYPHENYL 2-METHYLPROPANOATE
(E)-4-DECENAL
(+−)-2-ETHYL-4-(2,2,3-TRIMETHYL-3-CYCLOPENTEN-1-YL)-2-BUTEN-1-OL

TABLE A-continued high impact perfume raw materials having a Log T < −4
Perfume raw materials (Log T < −4)

(1R,5R)-4,7,7-TRIMETHYL-6-THIABICYCLO[3.2.1]OCT-3-ENE (A) +
(1R,4R,5R)-4,7,7-TRIMETHYL-6-THIABICYCLO[3.2.1]OCTANE
(B)
(−)-(3R)-3,7-DIMETHYL-1,6-OCTADIEN-3-OL
(E)-3-PHENYL-2-PROPENENITRILE
4-METHOXYBENZYL ACETATE
(E)-3-METHYL-5-(2,2,3-TRIMETHYL-3-CYCLOPENTEN-1-YL)-4-
PENTEN-2-OL
ALLYL (3-METHYLBUTOXY)ACETATE (A) + (+−)-ALLYL (2-
METHYLBUTOXY)ACETATE
(+−)-(2E)-1-(2,6,6-TRIMETHYL-2-CYCLOHEXEN-1-YL)-2-BUTEN-
1-ONE
(1E)-1-(2,6,6-TRIMETHYL-1-CYCLOHEXEN-1-YL)-1-PENTEN-3-
ONE

According to an embodiment, perfume raw materials having a Log T<−4 are chosen in the group consisting of aldehydes, ketones, alcohols, phenols, esters lactones, ethers, epoxydes, nitriles and mixtures thereof.

According to an embodiment, perfume raw materials having a Log T<−4 comprise at least one compound chosen in the group consisting of alcohols, phenols, esters lactones, ethers, epoxydes, nitriles and mixtures thereof, preferably in amount comprised between 20 and 70% by weight based on the total weight of the perfume raw materials having a Log T<−4.

According to an embodiment, perfume raw materials having a Log T<−4 comprise between 20 and 70% by weight of aldehydes, ketones, and mixtures thereof based on the total weight of the perfume raw materials having a Log T<−4.

The remaining perfume raw materials contained in the oil-based core may have therefore a Log T>−4.

Non limiting examples of perfume raw materials having a Log T>−4 are listed in table B below.

TABLE B perfume raw materials having a Log T > −4
Perfume raw materials (Log T > −4)

ETHYL 2-METHYLBUTYRATE
(E)-3-PHENYL-2-PROPENYL
ACETATE
(+−)-8-SEC-BUTYLQUINOLINE (A) +
(+−)-6-SEC-BUTYLQUINOLINE
(+−)-3-(1,3-BENZODIOXOL-5-YL)-2-
METHYLPROPANAL
VERDYLE PROPIONATE
1-(OCTAHYDRO-2,3,8,8-
TETRAMETHYL-2-NAPHTALENYL)-
1-ETHANONE
METHYL 2-((1RS,2RS)-3-OXO-2-
PENTYLCYCLOPENTYL)ACETATE
(+−)-(E)-4-METHYL-3-DECEN-5-OL
2,4-DIMETHYL-3-CYCLOHEXENE-1-
CARBALDEHYDE
1,3,3-TRIMETHYL-2-
OXABICYCLO[2.2.2]OCTANE
TETRAHYDRO-4-METHYL-2-(2-
METHYL-1-PROPENYL)-2H-PYRAN
ALDEHYDE C 12
1-OXA-12-CYCLOHEXADECEN-2-
ONE (A) +1-OXA-13-
CYCLOHEXADECEN-2-ONE (B)
(+−)-3-(4-ISOPROPYLPHENYL)-2-
METHYLPROPANAL
ALDEHYDE C 11 LENIQUE
(+−)-2,6-DIMETHYL-7-OCTEN-2-OL
(+−)-2,6-DIMETHYL-7-OCTEN-2-OL

TABLE B-continued perfume raw materials having a Log T > −4
Perfume raw materials (Log T > −4)

ALLYL 3-
CYCLOHEXYLPROPANOATE
(Z)-3-HEXENYL ACETATE
(2RS,5SR)-5-METHYL-2-(2-
PROPANYL)CYCLOHEXANONE (A) +
(2RS,5RS)-5-METHYL-2-(2-
PROPANYL)CYCLOHEXANONE (B)
ALLYL HEPTANOATE
(1RS,2RS)-2-(2-METHYL-2-
PROPANYL)CYCLOHEXYL ACETATE
(A) + (1RS,2SR)-2-(2-METHYL-2-
PROPANYL)CYCLOHEXYL ACETATE
(B)
1,1-DIMETHYL-2-PHENYLETHYL
BUTYRATE
GERANYL ACETATE (A) + NERYL
ACETATE (B)
(+−)-1-PHENYLETHYL ACETATE
1,1-DIMETHYL-2-PHENYLETHYL
ACETATE
3-METHYL-2-BUTENYL ACETATE
ETHYL 3-OXOBUTANOATE (A) <=>
(2Z)-ETHYL 3-HYDROXY-2-
BUTENOATE (B)
8-P-MENTHANOL
8-P-MENTHANYL ACETATE (A) + 1-
P-MENTHANYL ACETATE (B)
(+−)-2-(4-METHYL-3-CYCLOHEXEN-1-
YL)-2-PROPANYL ACETATE
(+−)-2-METHYLBUTYL BUTANOATE
2-{(1S)-1-[(1R)-3,3-
DIMETHYLCYCLOHEXYL]ETHOXY}-
2-OXOETHYL PROPIONATE
3,5,6-TRIMETHYL-3-CYCLOHEXENE-
1-CARBALDEHYDE (A) + 2,4,6-
TRIMETHYL-3-CYCLOHEXENE-1-
CARBALDEHYDE (B)
2-CYCLOHEXYLETHYL ACETATE
ALDEHYDE C 8
ETHYL BUTANOATE
(+−)-(3E)-4-(2,6,6-TRIMETHYL-2-
CYCLOHEXEN-1-YL)-3-BUTEN-2-
ONE (A) + (3E)-4-(2,6,6-TRIMETHYL-
1-CYCLOHEXEN-1-YL)-3-BUTEN-2-
ONE (B);
1-[(1RS,6SR)-2,2,6-
TRIMETHYLCYCLOHEXYL]-3-
HEXANOL
1,3,3-TRIMETHYL-2-
OXABICYCLO[2.2.2]OCTANE
1,3,3-TRIMETHYL-2-
OXABICYCLO[2.2.2]OCTANE
ETHYL HEXANOATE
UNDECANAL
ALDEHYDE C 10
2-PHENYLETHYL ACETATE
(1S,2S,4S)-1,7,7-
TRIMETHYLBICYCLO[2.2.1]HEPTAN-
2-OL (A) + (1S,2R,4S)-1,7,7-
TRIMETHYLBICYCLO[2.2.1]HEPTAN-
2-OL (B)
(+−)-3,7-DIMETHYL-3-OCTANOL
1-METHYL-4-(2-
PROPANYLIDENE)CYCLOHEXENE
(+)-(R)-4-(2-METHOXYPROPAN-2-
YL)-1-METHYLCYCLOHEX-1-ENE
VERDYL ACETATE
(3R)-1-[(1R,6S)-2,2,6-
TRIMETHYLCYCLOHEXYL]-3-
HEXANOL (A) + (3S)-1-[(1R,6S)-2,2,6-
TRIMETHYLCYCLOHEXYL]-3-
HEXANOL (B) + (3R)-1-[(1S,6S)-2,2,6-
TRIMETHYLCYCLOHEXYL]-3-
HEXANOL (C)

TABLE B-continued perfume raw materials having a Log T > −4
Perfume raw materials (Log T > −4)

(+)-(1S,1'R)-2-[1-(3',3'-DIMETHYL-1'-
CYCLOHEXYL)ETHOXY]-2-
METHYLPROPYL PROPANOATE

According to an embodiment, the oil phase (or the oil-based core) comprises 2-75 wt % of a density balancing material having a density greater than 1.07 g/cm$^3$ and 25-98 wt % of a perfume oil comprising at least 15 wt % of high impact perfume raw materials having a Log T<−4.

The density of a component is defined as the ratio between its mass and its volume (g/cm$^3$).

Several methods are available to determine the density of a component.

One may refer for example to the ISO 298:1998 method to measure d20 densities of essential oils.

According to an embodiment, the density balancing material is chosen in the group consisting of benzyl salicylate, benzyl benzoate, cyclohexyl salicylate, benzyl phenylacetate, phenylethyl phenoxyacetate, triacetin, methyl and ethyl salicylate, benzyl cinnamate, and mixtures thereof.

According to a particular embodiment, the density balancing material is chosen in the group consisting of benzyl salicylate, benzyl benzoate, cyclohexyl salicylate and mixtures thereof.

According to a particular embodiment, the hydrophobic material is free of any active ingredient (such as perfume). According to this particular embodiment, it comprises, preferably consists of hydrophobic solvents, preferably chosen in the group consisting of isopropyl myristate, tryglycerides (e.g. Neobee® MCT oil, vegetable oils), D-limonene, silicone oil, mineral oil, and mixtures thereof with optionally hydrophilic solvents preferably chosen in the group consisting of 1,4 butanediol, benzyl alcohol, triethyl citrate, triacetin, benzyl acetate, ethyl acetate, propylene glycol (1,2-propanediol), 1,3-Propanediol, dipropylene glycol, glycerol, glycol ethers and mixtures thereof.

Process for Preparing a Core-Shell Microcapsule Slurry

A first object of the invention is therefore a process for preparing a mineralized core-shell microcapsule slurry comprising the steps of:
(i) dissolving at least one polyisocyanate having at least two isocyanate groups in an oil comprising a hydrophobic material, preferably a perfume oil, to form an oil phase;
(ii) preparing an aqueous solution of a charged emulsifier to form a water phase;
(iii) adding the oil phase to the water phase to form an oil-in-water emulsion;
(iv) applying conditions suitable to induce interfacial polymerization to form core-shell microcapsules in the form of a slurry;
(v) adsorption of at least one mineral precursor on the microcapsule shell;
(vi) applying conditions suitable to induce growth of a mineral layer on the microcapsule shell,
characterized in that the polyisocyanate is added in an amount less than 1% by weight based on the total weight of the slurry of step (iv).

In step (i) of the process, a polyisocyanate having at least two isocyanate groups is dissolved in an oil comprising a hydrophobic material as defined above.

According to a preferred embodiment of the invention, there is used an amount of between 10 and 60%, more preferably between 20 and 50% of oil in the process of the invention, these percentages being defined by weight relative to the total weight of the obtained microcapsule slurry of step iv).

Suitable polyisocyanates used according to the invention include aromatic polyisocyanate, aliphatic polyisocyanate and mixtures thereof. Said polyisocyanate comprises at least 2, preferably at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate. The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

According to the invention, the at least one polyisocyanate used in the process according to the invention is present in amount less than 1%, preferably between 0.1 and less than 1%, more preferably between 0.1 and 0.8%, even more preferably between 0.3 and 0.8% by weight based on the total weight of the microcapsule slurry of step (iv).

Indeed, it has been shown that microcapsules prepared from a limited amount of polyisocyanate show good performance in terms of deposition.

According to the invention, the polymeric shell is formed by interfacial polymerisation in the presence of a charged emulsifier.

The charged emulsifier is preferably comprised in an amount ranging from 0.1 to 5.0% by weight of the microcapsule slurry, preferably between 0.5 and 2 wt % of the microcapsule slurry.

According to the invention, the polymeric shell has a terminating charged functional surface on which a mineral precursor will be adsorbed. Different ways can be used to impart such charged surface on the polymeric shell.

According to a particular embodiment, the terminating charged functional surface is a anionic surface.

Emulsifier=Anionic Emulsifier

According to a first embodiment, the charged emulsifier is an anionic emulsifier and forms an anionic surface once the interfacial polymerization is completed.

The anionic emulsifier can be amphiphilic materials, colloidal stabilizers or biopolymers. According to an embodiment, the anionic emulsifier is selected from the group consisting of polyvinyl alcohol, polyvinyl pyrrolidone, gum acacia, casein, sodium caseinate, soy (protein), hydrolyzed soy protein, pea protein, milk protein, whey protein, pectin, sugar beet pectin, sericin, bovine serum albumin, gelatin, and mixtures thereof.

According to an embodiment, gum acacia is preferred.

According to a particular embodiment, the anionic surface (formed by the anionic emulsifier) is the anionic surface on which a mineral precursor will be adsorbed in step (v).

However, to improve the bonding of mineral precursor on the anionic surface, the process can further comprise an additional step before step (v) (biomineralization step) consisting of adding a polyelectrolyte scaffolding composed of oppositely-charged polyelectrolyte layers once the microcapsules are formed.

Thus, according to a particular embodiment, the polyelectrolyte scaffolding includes at least one cationic polyelectrolyte layer and at least one anionic polyelectrolyte layer, the terminating layer being an anionic polyelectrolyte layer to form the terminating anionic functional surface of the shell.

According to this embodiment, the first layer of the polyelectrolyte scaffolding is a cationic polyelectrolyte layer deposited on the anionic surface (formed by the anionic emulsifier) and the last layer of the polyelectrolyte scaffolding is an anionic polyelectrolyte layer to form the terminating anionic functional surface on which a mineral precursor will be adsorbed in step (v).

The number of layers of the polyelectrolyte scaffolding is not particularly limited.

According to a particular embodiment, the polyelectrolyte scaffolding consists of two pairs of oppositely charged polyelectrolyte layers.

It means that according to this embodiment, before step (v), the microcapsule according to the invention comprises the following successive layers on the polymeric shell: a first cationic polyelectrolyte layer on the anionic surface (formed by the anionic emulsifier), a first negative polyelectrolyte layer, a second cationic polyelectrolyte layer, a second negative polyelectrolyte layer (forming the terminating anionic functional surface).

Additional layers can be used to impart barrier properties and can be additionally cross-linked.

Emulsifier=Cationic Emulsifier

According to a second embodiment, the charged emulsifier is a cationic emulsifier that forms a cationic surface when the interfacial polymerization is completed. According to an embodiment, the process comprises a further step of coating at least one anionic polyelectrolyte layer on the cationic surface to form core-shell microcapsule having an anionic functional surface.

According to an embodiment, the cationic emulsifier is obtained by mixing a weakly anionic emulsifier (such as PVOH) with a strongly charged cationic polymer or polyquaternium (such as Salcare® SC-60 by BASF).

As non-limiting examples of cationic emulsifiers, one may cite for example cationic functionalized polyvinyl alcohol (as an example, cationic C-506 by Kuraray) or chitosan at an appropriate pH (typically at a weakly acidic pH (approximately pH 6.5).

According to a particular embodiment, the anionic surface (formed by the anionic polyelectrolyte layer) is the terminating anionic functional surface on which a mineral precursor is adsorbed in step (v).

According to another embodiment, at least one cationic polyelectrolyte layer and at least a second anionic polyelectrolyte layer are deposited successively on the anionic polyelectrolyte layer.

However, this embodiment is not limited to only one pair of opposite polyelectrolyte layers but includes 2, 3, 4 or even more of pair of opposite polyelectrolyte layers. The charge of the last layer drives the charge of the mineral precursor added in step (v).

According to an embodiment, the cationic polyelectrolyte layer is chosen in the group consisting of poly(allylamine hydrochloride), poly-L-lysine and chitosan.

According to another embodiment, the anionic polyelectrolyte layer is chosen in the group consisting of poly (sodium 4 styrene sulfonate) (PSS), polyacrylic acid, polyethylene imine, humic acid, carrageenan, gum acacia, and mixtures thereof.

According to a particular embodiment, the anionic polyelectrolyte layer is PSS.

No specific action is required to induce interfacial polymerization. Preferably, the emulsion obtained is step iii) is maintained under stirring for 2 to 15 hours, preferably for 2 to 10 hours.

To increase the reaction kinetics, the stirring can be made at a pH comprised between 7 and 10 and/or at a temperature comprised between 50° C. and 70° C.

According to an embodiment, microcapsules according to the present invention are polyurea-based capsules. According to this particular embodiment, interfacial polymerization is induced by addition of a polyamine reactant in the dispersing phase to form a polyurea wall with a polyisocyanate present in the oil phase. The amine is preferably chosen in the group consisting of guanidine salts, tris-(2-aminoethyl)amine, N,N,N',N'-tetrakis(3-aminopropyl)-1,4-butanediamine, guanazole, amino acids such as lysine, amino alcohol such as 2-amino-1,3-propanediol, ethanolamine and mixtures thereof.

According to another embodiment, polyurea-based capsules are formed in absence of added polyamine reactant, and result only from the autopolymerization of the at least one polyisocyanate.

According to another embodiment, microcapsules according to the present invention are polyurethane-based capsules. According to this particular embodiment, interfacial polymerization is induced by the presence of a polyol in the water phase.

Preferably the polyol reactant is selected from the group consisting of monomeric and polymeric polyols with multiple hydroxyl groups available for reaction and mixtures thereof.

According to another embodiment, capsules according to the present invention are polyurea/polyurethane based. In that case, interfacial polymerization is induced by addition of a mixture of the reactant mentioned under both precedent embodiments. Additionally, crosslinkers with both amino groups and hydroxyl groups can be used to generate polyurea/polyurethane materials. Furthermore, polyisocyanates with both urea and urethane functionalities can be used to generate polyurea/polyurethane materials.

Prior to step (v), depending on the nature of the mineral precursor, microcapsules can be rinsed to remove the excess of emulsifier. Microcapsules can be rinsed for example by centrifugation and resuspended in water after withdrawing the supernatant.

Without being bound by theory, it is believed that the charged surface of the shell is providing functional anchoring sites and a high local density of charge groups and nucleation sites onto the surface of the microcapsules resulting in improved adsorption of mineral precursor species followed by initiation of the mineral growth process through in-situ addition of a precipitating species.

According to an embodiment, mineral precursors are adsorbed to the surface of microcapsules by incubating the charged capsules in at least one solution containing oppositely charged mineral precursor, providing sufficient agitation and time to allow for complete coverage of capsule surfaces. Removal of excess precursor from solution to prevent generation of free mineral material in solution can be done and is followed by initiation of the mineral growth process through in-situ addition of a precipitating species.

The person skilled in the art will be able to select suitable conditions for the mineral growth process (for example, precursor selection, reaction conditions, the solution concentrations, incubation times, agitation speeds, temperatures and pH conditions).

Typically:
  mineralization can occur at room temperature,
  incubation of precursor can take place from 1-72 hours depending on the nature of the mineral precursor,
  the nature of the precipitation species depends on the nature of the precursor.

According to a particular embodiment, the mineral precursor solution is chosen in the group consisting of an iron (II) sulfate solution (comprising iron ions as precursor), an iron (III) chloride solution (comprising iron ions as precursor), calcium-based salt solution (comprising calcium ions as precursor), phosphate-based salt solution (comprising phosphate ions as precursor), carbonate-based salt solution (comprising carbonate ions as precursor), titanium-based precursor solution, zinc-based precursor solution, and mixtures thereof.

One may cite for example titanium alkoxides as titanium-based precursor or zinc alkoxides, zinc acetate, zinc chloride as zinc-based precursor solution.

According to a particular embodiment, the mineral precursor solution is chosen in the group consisting of an iron (II) sulfate solution (comprising iron ions as precursor), an iron (III) chloride solution (comprising iron ions as precursor), calcium-based salt solution (comprising calcium ions as precursor), phosphate-based salt solution (comprising phosphate ions as precursor) and mixtures thereof.

The water-soluble calcium-based salt can be chosen in the group consisting of calcium chloride ($CaCl_2$), calcium nitrate ($Ca(NO_3)_2$), calcium bromide ($CaBr_2$), calcium iodide ($CaI_2$), calcium chromate ($CaCrO_4$), calcium acetate ($CaCH_3CO_2$) and mixtures thereof. Most preferred are calcium chloride and calcium nitrate.

The water-soluble phosphate-based salt can be chosen in the group consisting of sodium phosphate (monobasic) ($NaH_2PO_4$), sodium phosphate (dibasic) ($Na_2HPO_4$), sodium phosphate (tribasic): $Na_3PO_4$, potassium phosphate (monobasic): $KH_2PO_4$, potassium phosphate (dibasic) ($K_2HPO_4$), potassium phosphate (tribasic) ($K_3PO_4$), ammonium phosphate (monobasic) (($NH_4)H_2PO_4$), ammonium phosphate(dibasic) (($NH_4)_2HPO_4$), ammonium phosphate (tribasic) (($NH_4)_3PO_4$) and mixtures thereof.

The water-soluble carbonate-based salt can be chosen in the group consisting of sodium, potassium and ammonium based carbonates.

It should be understood that the charge of the mineral precursor used in step (v) of the process is driven by the charge of the terminating surface of the microcapsules.

Embodiment 1

According to an embodiment, the mineral precursor solution is chosen in the group consisting of an iron (II) sulfate solution, or an iron (III) chloride solution.

As said previously, the initiation of the mineral growth process can be done through in-situ addition of a precipitating species. According to this embodiment, when the mineral precursor is an iron solution, irons ions are adsorbed on the anionic surface of the shell and precipitating species used is a base for hydrolysis to form an iron oxide layer (for example by addition of a sodium hydroxide solution).

The weight ratio between the mineral precursor salt in solution and the microcapsules slurry of step iv) can be comprised between 1:1 and 2:1, preferably between 1.3:1 and 1.7:1, and most preferably between 1.5:1 and 1.6:1. Values are given for pure salts in solution—the person skilled in the art will be able to adapt the amount of the salt if a hydrated form is used.

Embodiment 2

According to another embodiment, the mineral precursor solution is a calcium-based salt (comprising calcium ions as precursor). According to this embodiment, calcium ions are adsorbed on the anionic surface. Precipitating species that will induce the mineral precipitation in that case is the addition of another salt, preferably a phosphate-based salt (for one hour for example).

Thus, according to this particular embodiment, microcapsules are introduced sequentially or simultaneously in at least two solutions comprising respectively at least one precursor. Preferably, the first solution comprises water-soluble calcium-based salt including a calcium precursor (first mineral precursor of step v)) and the second solution comprises water-soluble phosphate-based salt including a phosphate precursor (second mineral precursor to induce the mineral growth of the mineral layer). Addition order could change according to the selection and charge of the underlying terminating layer.

According to a particular embodiment, the first solution comprises calcium nitrate ($Ca(NO_3)_2$) and the second solution comprises sodium phosphate (dibasic) ($Na_2HPO_4$).

According to another particular embodiment, the first solution comprises calcium chloride ($CaCl_2$) and the second solution comprises sodium phosphate carbonate ($Na_2CO_3$). To improve the robustness of the shell, microcapsules can be then incubated again several times simultaneously or sequentially in the two mineral precursor solutions.

Embodiment 3

Still according to another embodiment, when the terminating surface of the microcapsules are cationic, the microcapsules are firstly incubating in carbonate-based salt solution or in a phosphate-based salt solution to adsorb carbonate ions $CO_3^{2-}$ or phosphate ions $PO_4^{3-}$ respectively on the cationic surface followed by an incubation in a calcium-based mineral solution.

To improve the robustness of the shell, microcapsules can be then incubated again several times simultaneously or sequentially in the two mineral precursor solutions.

According to different embodiments described above, the weight ratio between the first mineral precursor salts in solution and the microcapsules slurry of step iv) can be comprised between 0.01:1 and 0.5:1, more preferably between 0.03:1 and 0.4:1, and the weight ratio between the second mineral precursor solution and the microcapsules slurry of step iv) can be comprised between 0.01:1 and 0.5:1, preferably between 0.03:1 and 0.4:1.

According to a particular embodiment, the weight ratio between the first mineral precursor salts in solution and the microcapsules slurry of step iv) can be comprised between 0.1:1 and 0.5:1, preferably between 0.15:1 and 0.4:1, and the weight ratio between the second mineral precursor solution and the microcapsules slurry of step iv) can be comprised between 0.05:1 and 0.3:1, preferably between 0.08:1 and 0.25:1. Values are given for pure salts in solution—the person skilled in the art will be able to adapt the amount of the salt if a hydrated form is used.

According to the different embodiments described above, once a mineral layer is formed, one may repeat the biomineralization step with other mineral precursors so as to form at least a second mineral layer different from the first mineral layer. Polyelectrolyte layers can be formed between the mineral layers.

According to a particular embodiment of the invention, at the end of step vi) one may also add to the invention's slurry a polymer selected from the group consisting of a polysaccharide, a biopolymer, a cationic polymer and mixtures thereof to form an outer coating to the microcapsule.

Polysaccharide polymers are well known to a person skilled in the art. Preferred polysaccharides are selected from the group consisting of locust bean gum, xyloglucan, guar gum, hydroxypropyl guar, hydroxypropyl cellulose and hydroxypropyl methyl cellulose.

According to a particular embodiment, the coating consists of a cationic coating.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 2M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C135 or C17, origin Rhodia).

Depending on the charge of the mineralized microcapsules surface, and solution conditions (including pH), an anionic polyelectrolyte can be first adsorbed on the surface followed by the adsorption of a cationic polymer. Or, a cationic polymer could be adsorbed followed by adsorption of an anionic coating.

Post-functionalization of the mineralized shell could be done to impart greater barrier functionality, to serve as a foundation for further enzymatic crosslinking, to serve as a foundation for further mineralization, or to offer a differently functionalized surface to facilitate compatability with application bases or performance (such as deposition performance) from application bases.

According to any one of the above embodiments of the invention, there is added an amount of polymer described above comprised between about 0% and 5% w/w, or even between about 0.1% and 2% w/w, percentage being expressed on a w/w basis relative to the total weight of the slurry as obtained after step vi). It is clearly understood by a person skilled in the art that only part of said added polymers will be incorporated into/deposited on the microcapsule.

Multiple Microcapsules System

According to an embodiment, the microcapsules of the invention (first microcapsule slurry) can be used in combination with a second microcapsules slurry.

Another object of the invention is a microcapsule delivery system comprising:
  the microcapsule slurry of the present invention as a first microcapsule slurry, and
  a second microcapsule slurry, wherein the microcapsules contained in the first microcapsule slurry and the second microcapsule slurry differ in their hydrophobic material and/or their wall material and/or in their mineral layer and/or in their coating material.

As non-limiting examples, the nature of the polymeric shell of the second microcapsules slurry of the invention can vary. As non-limiting examples, the shell of the second microcapsules slurry can be aminoplast-based, polyurea-based or polyurethane-based. The shell of the second microcapsules slurry can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell of the second microcapsules slurry comprises an aminoplast copolymer, such as melamine-formaldehyde or urea-formaldehyde or cross-linked melamine formaldehyde or melamine glyoxal.

According to another embodiment the shell of the second microcapsules slurry is polyurea-based made from, for example but not limited to isocyanate-based monomers and amine-containing crosslinkers such as guanidine carbonate and/or guanazole. Preferred polyurea microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). According to another embodiment, the emulsifier is an anionic or amphiphilic biopolymer preferably chosen from the group consisting of gum Arabic, soy protein, gelatin, sodium caseinate and mixtures thereof.

According to another embodiment, the shell of the second microcapsules slurry is polyurethane-based made from, for example but not limited to polyisocyanate and polyols, polyamide, polyester, etc.

The preparation of an aqueous dispersion/slurry of core-shell microcapsules is well known by a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the second core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together
  a) a polyamine component in the form of melamine or of a mixture of melamine and at least one $C_1$-$C_4$ compound comprising two $NH_2$ functional groups;
  b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
  c) a protic acid catalyst;

2) preparing an oil-in-water dispersion, wherein the droplet size is comprised between 1 and 600 um, and comprising:
  i. an oil;
  ii. a water medium
  iii. at least an oligomeric composition as obtained in step 1;
  iv. at least a cross-linker selected amongst
  A) $C_4$-$C_{12}$ aromatic or aliphatic di- or tri-isocyanates and their biurets, triurets, trimmers, trimethylol propane-adduct and mixtures thereof; and/or
  B) a di- or tri-oxiran compounds of formula

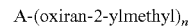

wherein n stands for 2 or 3 and 1 represents a $C_2$-$C_6$ group optionally comprising from 2 to 6 nitrogen and/or oxygen atoms;
  v. optionally a $C_1$-$C_4$ compounds comprising two $NH_2$ functional groups;
3) Heating said dispersion;
4) Cooling said dispersion.

This process is described in more details in WO 2013/068255, the content of which is included by reference.

According to another embodiment, the shell of the of the second microcapsules slurry is polyurea- or polyurethane-based. Examples of processes for the preparation of polyurea and polyureathane-based microcapsule slurry are for instance described in WO2007/004166, EP 2300146, EP2579976 the contents of which is also included by reference. Typically a process for the preparation of polyurea or polyurethane-based microcapsule slurry include the following steps:
  a) Dissolving at least one polyisocyanate having at least two isocyanate groups in an oil to form an oil phase;
  b) Preparing an aqueous solution of an emulsifier or colloidal stabilizer to form a water phase;
  c) Adding the oil phase to the water phase to form an oil-in-water dispersion, wherein the mean droplet size is comprised between 1 and 500 μm, preferably between 5 and 50 μm;
  d) Applying conditions sufficient to induce interfacial polymerisation and form microcapsules in form of a slurry.

Process for Preparing a Mineralized Microcapsules Powder

Another object of the invention is a process for preparing a mineralized microcapsules powder comprising the steps as defined above for the preparation of a microcapsule slurry and an additional final step consisting of submitting the microcapsule slurry to a drying, like lyophilisation or spray-drying, to provide the microcapsules as such, i.e. in a powder form. It is understood that any standard method known by a person skilled in the art to perform such drying is applicable. In particular the slurry may be spray-dried preferably in the presence of a polymeric carrier material such as polyvinyl acetate, polyvinyl alcohol, dextrins, maltodextrin, natural or modified starch, sugars, gum Arabic, vegetable gums such as gum acacia, pectins, xanthans, alginates, carrageenans or cellulose derivatives to provide microcapsules in a powder form. Preferably, the carrier is a gum Acacia. According to a particular embodiment, the carrier material contains free perfume oil which can be same or different from the perfume from the core of the microcapsules.

Microcapsule Slurry/Microcapsule Powder

Another object of the invention is a mineralized core-shell microcapsule slurry comprising at least one microcapsule made of:
  an oil-based core;
  a polyurea shell or a polyurethane shell, and a mineral layer.

According to an embodiment, the polyurea or the polyurethane shell comprises less than 1% by weight of a polyisocyanate having at least two isocyanate groups based on the total weight of the slurry.

According to an embodiment, the mineral layer comprises a material chosen in the group consisting of iron oxides, iron oxyhydroxide, titanium oxides, zinc oxides, calcium carbonates, calcium phosphates and mixtures thereof. Preferably, the mineral layer is an iron oxide, an iron oxyhydroxide, or a calcium phosphate or a calcium carbonate. All crystalline minerals, amorphous minerals and mineral polymorphs (such as hydroxyapatite for calcium phosphate; and calcite, vaterite, and aragonite for calcium carbonate) are included.

According to a particular embodiment, the mineral layer is iron oxyhydroxide goethite ($\alpha$-FeO(OH)).

According to another embodiment, the mineral layer is calcium phosphate.

According to another embodiment, the mineral layer is calcium carbonate.

According to another embodiment, multiple mineral layers comprising calcium phosphate and calcium carbonate are present on the microcapsule.

According to a particular embodiment, the mineral layer does not comprise silicon oxides.

According to another embodiment, the microcapsules can comprise a polyelectrolyte, a biopolymer or cationic coating on the mineral layer, followed optionally by a second mineral layer.

Another object of the invention is a mineralized core-shell microcapsule slurry obtainable by the process as defined above.

Perfuming Composition

Another object of the invention is a perfuming composition comprising
 (i) microcapsules as defined above, wherein the oil-based core comprises a perfume;
 (ii) at least one ingredient selected from the group consisting of a perfumery carrier and a perfuming co-ingredient; and
 (iii) optionally a perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.05 to 40%, preferably between 0.1 and 40% by weight of microcapsules as defined above.

Consumer Product

The microcapsules of the invention can be used in combination with active ingredients.

An object of the invention is therefore a composition comprising:
 (i) microcapsules as defined above;
 (ii) an active ingredient, preferably chosen in the group consisting of a cosmetic ingredient, skin caring ingredient, perfume ingredient, flavor ingredient, malodour counteracting ingredient, bactericide ingredient, fungicide ingredient, pharmaceutical or agrochemical ingredient, a sanitizing ingredient, an insect repellent or attractant, and mixtures thereof.

The invention's microcapsules can advantageously be used in many application fields and used in consumer products. Microcapsules can be used in liquid form applicable to liquid consumer products as well as in powder form, applicable to powdered consumer products.

A consumer product, preferably in the form of a laundry care product, a home care product, a body care product, a skin care product, a hair care product, an air care product, or a hygiene product, comprising microcapsules as defined above, or a perfuming composition as defined above is also an object of the present invention.

Another object of the present invention is a liquid consumer product comprising:
a) from 2 to 65% by weight, relative to the total weight of the consumer product, of at least one surfactant;
b) water or a water-miscible hydrophilic organic solvent; and
c) microcapsule slurry as defined above,
d) optionally non-encapsulated perfume.

A powdered consumer product comprising
 (a) from 2 to 65% by weight, relative to the total weight of the consumer product, of at least one surfactant;
 (b) microcapsule powder as defined above.

(c) optionally perfume powder that is different from the microcapsules defined above is also an object according to the present invention.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

In particular a liquid consumer product comprising:
a) from 2 to 65% by weight, relative to the total weight of the consumer product, of at least one surfactant;
b) water or a water-miscible hydrophilic organic solvent; and
c) a perfuming composition as defined above is another object of the invention.

Also a powdered consumer product comprising:
(a) from 2 to 65% by weight, relative to the total weight of the consumer product, of at least one surfactant; and
(b) a perfuming composition as defined above is part of the invention.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumery consumer product can be a perfume, such as a fine perfume, a cologne or an after-shave lotion; a fabric care product, such as a liquid or solid detergent, tablets and pods, a fabric softener, a dryer sheet, a fabric refresher, an ironing water, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.), a hygiene product such as sanitary napkins, diapers, toilet paper.

According to a particular embodiment, the consumer product is selected from the group consisting of a shampoo, a shower gel, a rinse-off conditioner, a soap bar, a powder or a liquid detergent, a fabric softener and a floor cleaner.

According to a preferred embodiment, the consumer product is a shampoo or a rinse-off conditioner. According to another preferred embodiment, the product is a perfumed soap. According to another preferred embodiment, the product is a body wash. According to another preferred embodiment, the product is a fabric care product.

According to a particular embodiment, the consumer product is in the form of a fabric softener composition and comprises:

between 85 and 99.9% of a fabric softener active base;

between 0.1 to 15 wt %, more preferably between 0.2 and 5 wt % by weight of the microcapsule slurry of the invention.

The fabric softener active base may comprise cationic surfactants of quaternary ammonium, such as Diethyl ester dimethyl ammonium chloride (DEEDMAC), TEAQ (triethanolamine quat), HEQ (Hamburg esterquat).

According to a particular embodiment, the consumer product is in the form of a perfuming composition comprising:

0.1 to 20% of microcapsules as defined previously, 0 to 40%, preferably, 3-40% of perfume, and 30 to 90%, preferably 40-90% of ethanol, by weight based on the total weight of the perfuming composition.

Preferably, the consumer product comprises from 0.05 wt %, preferably from 0.1 to 15 wt %, more preferably between 0.2 and 5 wt % of the microcapsules of the present invention, these percentages being defined by weight relative to the total weight of the consumer product. Of course the above concentrations may be adapted according to the olfactive effect desired in each product.

Method for Depositing Microcapsules on a Surface

The mineral layer on microcapsule shell is surprisingly significantly boosting the deposition efficiency and retention of microcapsules on targeted surfaces such as hair and fabric. When microcapsules are applied on a substrate, the percentage of deposition is much higher than that of known delivery systems.

Thus, another object of the invention is a method for depositing microcapsules on a surface, which comprises treating said surface with a perfuming composition as defined above or a consumer product as defined above.

The capsules of the invention have proven to be particularly useful in rinse-off application as their deposition is much superior to delivery systems known heretofore.

The invention will now be further described by way of examples. It will be appreciated that the invention as claimed is not intended to be limited in any way by these examples.

EXAMPLES

Example 1

Preparation of Mineral Coated Polyurea-Based Capsules According to the Invention Polyurea microcapsules were synthesized according to the formulation described in Table 1 (microcapsules A or C) or Table 2 (microcapsules B or D), and loaded with a perfume oil A outlined in Table 3. These microcapsules were then subjected to sequential additions of mineral precursors as described in this example.

TABLE 1

Composition of capsules A or capsules C according to the invention prior to mineralization

| Ingredient | Percentage |
| --- | --- |
| Perfume Oil [1] | 38.0 |
| Uvinul A Plus [2] | 2.0 |
| Takenate ® D-110N [3] | 0.8 |
| Gum Arabic [4] | 1.0 |
| Water | 58.2 |

[1] Perfuming composition described in Table 3.
[2] Tracer for the quantification of oil deposition
[3] Trimethylol propane adduct of xylylene diisocyanate; origin: Mitsui Chemicals 75% polyisocyanate/25% ethyl acetate
[4] SuperStab AA ®; origin: Nexira Inc., Somerville, NJ

TABLE 2

Composition of capsules B or capsules D according to the invention prior to mineralization

| Ingredient | Percentage |
| --- | --- |
| Perfume Oil [1] | 38.0 |
| Uvinul A Plus [2] | 2.0 |
| Takenate ® D-110N [3] | 0.4 |
| Gum Arabic [4] | 1.0 |
| Water | 58.6 |

[1] Perfuming composition described in Table 3.
[2] Tracer for the quantification of oil deposition
[3] Trimethylol propane adduct of xylylene diisocyanate; origin: Mitsui Chemicals 75% polyisocyanate/25% ethyl acetate
[4] SuperStab AA ®; origin: Nexira Inc., Somerville, NJ

TABLE 3

Perfume oil A composition

| Chemical name | Amount (% wt) |
| --- | --- |
| Isopropyl myristate | 0.3 |
| (Z)-3-hexen-1-ol butyrate | 0.6 |
| Delta damascone | 1.0 |
| 2,4-Dimethyl-3-cyclohexene-1-carbaldehyde | 1.0 |
| Habanolide ® 1) | 3.0 |
| Hedione ® 2) | 5.0 |
| Hexyl cinnamic aldehyde | 12.0 |
| Iso E Super ®3) | 16.0 |
| Verdyl acetate | 24.0 |
| Lilial ®4) | 37.0 |

1) Trademark from Firmenich; pentadecenolide, origin: Firmenich SA, Geneva, Switzerland
2) Trademark from Firmenich; Methyl-cis-3-oxo-2-pentyl-1-cyclopentane acetate, origin: Firmenich SA, Geneva, Switzerland
3) Trademark from IFF; 7-acetyl, 1,2,3,4,5,6,7,8-octahydro-1,1,6,7-tetramethyl naphthalene
4) Trademark from Givaudan; 3-(4-tert-butylphenyl)-2-methylpropanal At least one polyisocyanate (e.g. Trimethylol propane adduct of xylylene diisocyanate Takenate® D-110N) was dissolved in a perfume oil (with Uvinul A Plus tracer). The oil phase was then added to an aqueous emulsifier solution (e.g. gum Arabic) and homogenized for 3 min using an Ultra-Turrax T25 disperser at 20000 rpm to form an O/W emulsion. This emulsion was then stirred at 500 rpm using a mechanical overhead stirrer. Then, the reaction temperature was gradually elevated to 70° C. over 1 h and was maintained at 70° C. for 2 h before being allowed to cool to room temperature.

A core-shell microcapsule slurry is obtained.

15 g of the microcapsule slurry is diluted in 135 g of an alkaline buffer solution (pH 9) and 4.5 mL of 0.3 molar calcium nitrate solution is added. The mixture is stirred by anchor stirrer in a closed reactor at 250 rpm until the calcium ions have sufficient time to interact with the anionic surface of the microcapsules.

(i) 4.5 mL of a 0.18 molar solution of dibasic sodium phosphate is added slowly by syringe pump over 60 minutes (75 μL/min) to initiate the nucleation of mineral material at the capsule surface by precipitating the calcium cations with the phosphate anions followed by an additional 60 minutes of stirring.

(ii) Equal 7.5 mL volumes of 0.3 molar calcium nitrate and 0.18 molar sodium phosphate solutions are then simultaneously slowly added by syringe pump over 60 minutes (125 μL/min each) followed by an hour of stirring to allow for further mineral precipitation.

(iii) Equal 30 mL volumes of 0.3 molar calcium nitrate and 0.18 molar sodium phosphate solutions are then slowly added over 60 minutes (500 μL/min) simultaneously followed by 60 minutes of stirring to allow for further mineral precipitation. This process is repeated once again to generate a robust mineral shell in this example. The additions could be repeated systematically to achieve the desired mineral shell thickness and properties

TABLE 4

Mineralization Parameters for Nucleation and Growth of Calcium Phosphate Based Mineral Layer

| Parameter | Precursor 1 Addition | Precursor 2 Addition |
| --- | --- | --- |
| Reactant | $Ca(NO_3)_2$ | $Na_2HPO_4$ |
| Amount | 5.1 g | 3.47 g |
| Concentration | 0.3M | 0.18M |
| Volume | 72 mL | 72 mL |
| pH | 8.5 | 8.5 |
| Addition Time (hours) | 1 | 1 |
| Temperature (° C.) | RT (22) | RT (22) |
| Mixing Speed (rpm) | 250 | 250 |

Example 2

Preparation of Polyurea-Based Control Capsules According to the Invention (X)

Control microcapsules X were prepared using a similar protocol as described in Example 1 with a composition as reported in Table 5, except that the control capsules are unmodified (i.e without mineralization).

TABLE 5

Composition of capsules A according to the invention prior to mineralization

| Ingredient | Percentage |
|---|---|
| Perfume Oil [1] | 38.0 |
| Uvinul A Plus [2] | 2.0 |
| Takenate ® D-110N [3] | 5.1 |
| Gum Arabic [4] | 1.0 |
| Water | 53.9 |

[1] Perfuming composition described in Table 3.
[2] Tracer for the quantification of oil deposition
[3] Trimethylol propane adduct of xylylene diisocyanate; origin: Mitsui Chemicals
[4] SuperStab AA ®; origin: Nexira Inc., Somerville, NJ

Example 3

Capsules Characterization and Deposition Results

Microscopy of Capsules:

To image the microcapsules, dilute capsule slurries were dried onto carbon tape, which was adhered to aluminium stubs and then sputter coated with a gold/palladium plasma. The stubs were placed into a scanning electron microscope (JEOL 6010 PLUS LA) for analysis. Images of Capsule A and Capsule B are shown respectively in FIG. 1, FIG. 2, FIG. 3, FIG. 4 to illustrate that stable, robust, rough mineralized microcapsules can be generated by growing a spinulose mineral coating onto smooth polyurea microcapsule scaffolds.

Figure 5:
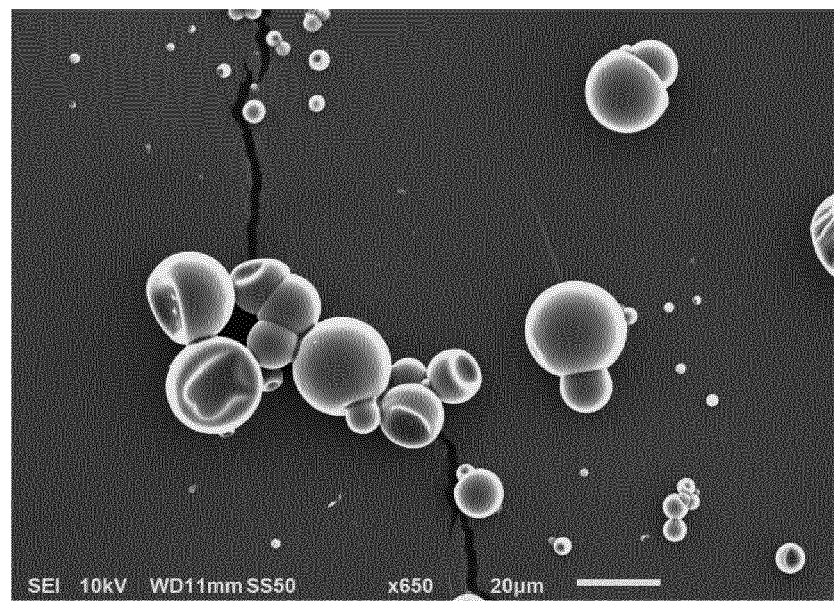
FIG. 5 represents scanning electron micrographs of comparative unmineralized microcapsules (Capsules X).

By contrast, comparative microcapsules X have a smooth, unmodified surface (FIG. 5).

Figure 6:
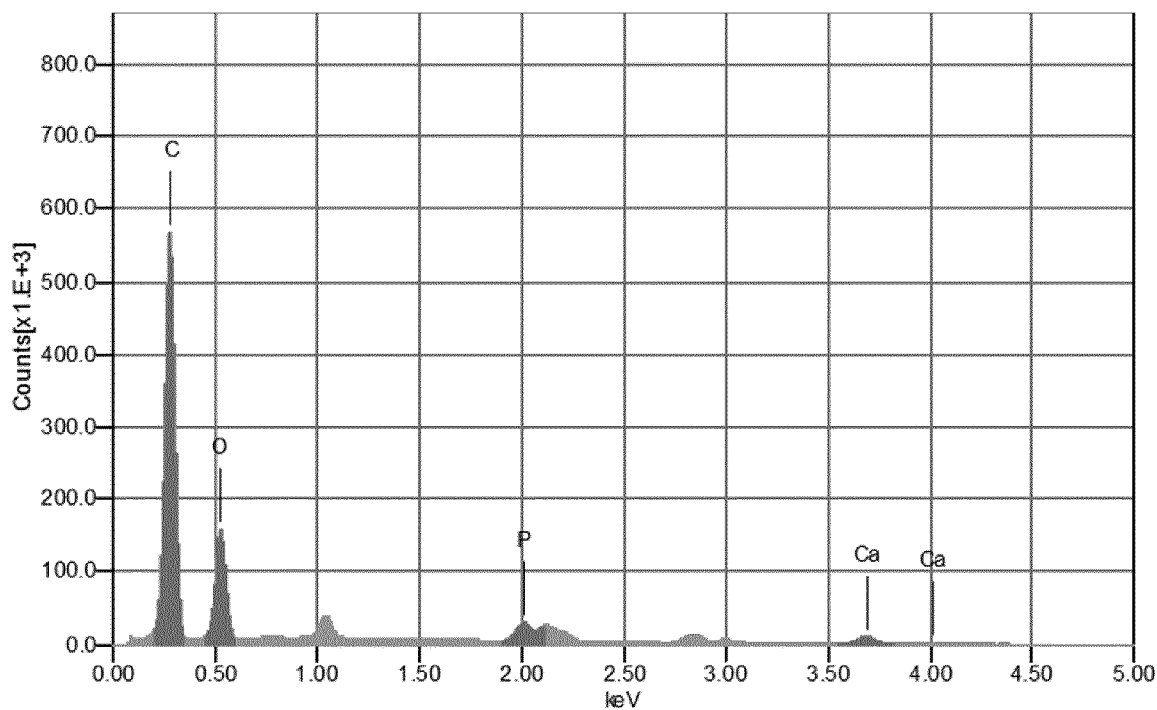
FIG. 6 represents energy dispersive spectroscopy (EDS) of the microcapsules according to the invention.

Energy dispersive spectroscopy performed on microcapsules A confirms the elemental presence of calcium (Ca) and phosphorus (P) in the composition of the calcium phosphate mineral coating (see FIG. 6) for oil-loaded capsules analysed off of carbon tape. Elemental mapping of elements oxygen (O), phosphorus (P), and calcium (Ca) compliments the EDS spectrum for a single capsule on a carbon taped stub has been carried out and confirms the presence of a mineral coating.

TABLE 6

Energy dispersive spectrograph

| Element | Mass % | Atom % | Sigma | Net | K ratio | Line |
|---|---|---|---|---|---|---|
| C | 65.06 | 76.59 | 0.00 | 14115183 | 0.8639065 | K |
| O | 20.14 | 17.80 | 0.01 | 3971721 | 0.7149966 | K |
| P | 3.74 | 1.71 | 0.01 | 687181 | 0.1494995 | K |
| Ca | 11.07 | 3.91 | 0.03 | 510739 | 0.3020915 | K |
| Total | 100 | 100 | | | | |

Deposition Testing on Hair:

For the quantification of deposition, the following procedure was used. A 500 mg mini hair swatch was wet with 40 mL of tap water (37-39° C.) aimed at the mount with a 140 mL syringe. The excess water was gently squeezed out once and 0.1 mL of a model surfactant mixture containing microcapsules loaded with a UV tracer (Uvinul A Plus) was applied with a 100 μL positive displacement pipet. The surfactant mixture was distributed with 10 horizontal and 10 vertical passes. The swatch was then rinsed with 100 mL of tap water (37-39° C.) with 50 mL applied to each side of the swatch aimed at the mount. The excess water was gently squeezed out and the hair swatch was then cut into a pre-weighed 20 mL scintillation vial. This process was repeated 2 more times and then the vials containing the cut hair were dried in a vacuum oven @ 50-60° C. (100 Torr) for at least 5 hours. After the drying process, the vials were again weighed to determine the mass of the hair in the vials. Controls were also prepared by adding 0.1 mL of the model surfactant mixture containing capsules to an empty vial. 4 mL of 200-proof ethanol were then added to each vial and they were subjected to 60 minutes of sonication. After sonication, the samples were filtered through a 0.45 μm PTFE filter and analyzed with a HPLC using a UV detector. To determine the percent deposition of microcapsules from a model surfactant mixture, the amount of Uvinul extracted from the hair samples was compared to the amount of Uvinul extracted from the control samples.

TABLE 7

Model surfactant mixture

| Ingredients | Active Amount (% wt) | Function |
|---|---|---|
| Sodium Laurel Ether Sulfate (SLES) | 12 | Anionic Surfactant |
| Cocamidopropyl Betaine (CAPB) | 3 | Amphoteric Surfactant |
| Salcare ® SC 60 1) Polymer [1] | 0.5 | Deposition Aid |
| Water | 84 | Solvent |
| Microcapsule Slurry (Equivalent Oil) | 0.5 | Fragrance |

[1] acrylamidopropyltrimonium chloride/acrylamide copolymer; origin BASF

Deposition onto hair swatches was measured from this simplified model surfactant mixture which is meant to be representative of personal cleansing formulations such as shampoo or shower gel. Results are shown in FIG. 7.

Figure 7:
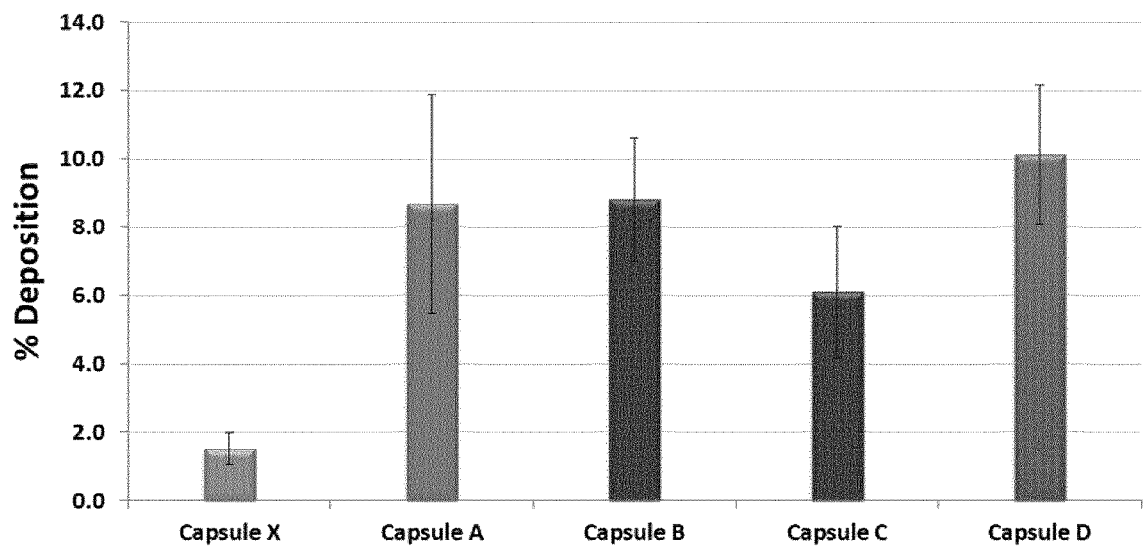
FIG. 7 represents the percentage of microcapsule deposition of mineralized microcapsules according to the invention (Capsules A, B, C and D) compared to smooth control capsules (Capsules X) onto hair from a model surfactant mixture.

The data illustrated in FIG. 7 demonstrate that the addition of a mineral layer to an anionic Gum Arabic-stabilized capsule increases the deposition onto hair swatches significantly from 1.8% for the control capsules X to more than 6% for the mineralized capsules A, capsules B, capsules C, and capsules D. The capsules according to the invention are boosting deposition up to 4 times better than prior art capsules.

Example 4

Thermogravimetric Profiles of Microcapsules of the Invention

Thermogravimetric analysis (TGA) was conducted on small samples (<50 mg) of each mineralized microcapsule slurry to determine relative microcapsule stability as well as the relative proportions of organic and inorganic solids content. This was conducted by placing the sample in a furnace, raising the temperature to and maintaining an isotherm at 50° C. for 250 minutes to drive off the aqueous portion of the slurry, then raising the temperature to 400° C. and maintaining an isotherm for 60 minutes to burn off the organic content, leaving the residual inorganic content behind.

Figure 8:
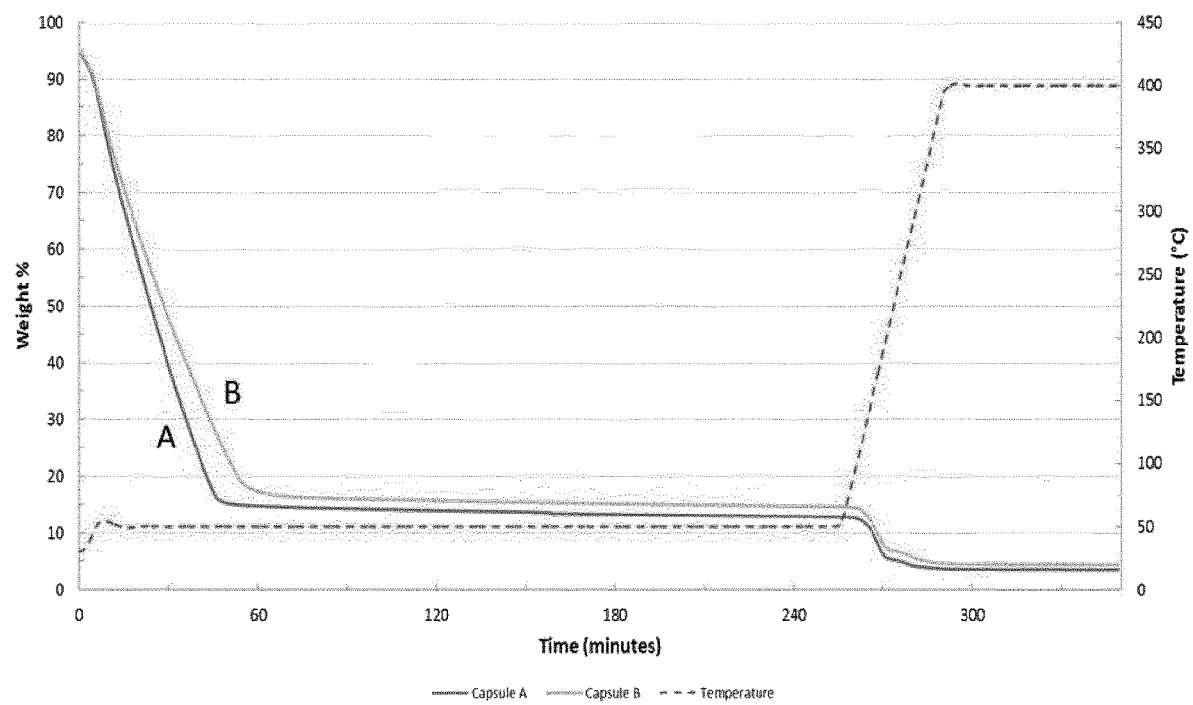
FIG. 8 represents thermogravimetric analysis of microcapsules.

FIG. 8 shows an initial plateau where the total solids content is given (organic and inorganic) as well as a secondary plateau showing the residual inorganic content after burning off the organic content (oil plus polymer). One can conclude from the initial plateau that microcapsules A and B demonstrate sufficient stability to contain the organic core material under elevated temperature for an extended time period. The TGA plateau behaviour during the isotherm at 50° C. for 250 minutes is indicative of longer term storage stability for both microcapsules A and B. Permeable, broken or unstable capsules are expected to lose the oil payload during the 250 minute isotherm step. Additionally, a significant fraction of the mineralized capsules is determined to be inorganic mineral material after the second 400° C. isotherm for 60 minutes.

Example 5

Stability of Microcapsules in a Fabric Softener Base and Shower Gel Base

Microcapsules A were tested for leakage stability in application base against a free oil control to determine the quantity of oil leaked from the capsules after exposure to elevated temperatures in base. The capsules were loaded at 0.5 wt % equivalent oil loadings into a fabric softener base (see Table 8) as well as a shower gel base (see Table 9) and placed into an oven at 37° C. and analyzed by SPME GC/MS after one week.

Protocol for the Stability Assessment

Weigh 1 g of sample into a 20 ml headspace vial and seal with a septum. Equilibrate the sample for 10 minutes at 65° C. Expose the SPME fiber to the vapor phase for 20 minutes at 65° C. Desorb the SPME fiber into a standard GC injector (splitless) for 5 minutes at 250° C. Analyze the components with an Agilent GCMS (5977B MSD, 7890B GC) or equivalent. All samples are compared to a free oil reference control which corresponds to 100% leakage.

TABLE 8

Fabric softener composition

| Product | Wt % |
|---|---|
| Stepantex VL 90A | 8.88 |
| Calcium Chloride Sol. 10% | 0.36 |
| Proxel GXL | 0.04 |
| Perfume | 1 |
| Water | 89.72 |
| TOTAL | 100 |

TABLE 9

Shower gel composition

| Ingredients | Amount (% wt) |
|---|---|
| Deionised water | 49.35 |
| EDETA B Powder[1] | 0.05 |
| Carbopol ® Aqua SF-1 polymer[2] | 6.00 |
| Zetesol AO 328 U[3] | 35.00 |
| Sodium hydroxide 20% aqueous solution | 1.00 |
| Tego ® Betain F 50[4] | 8.00 |
| Kathon CG | 0.10 |
| Citric acid 40% aqueous solution | 0.50 |

Figure 9:
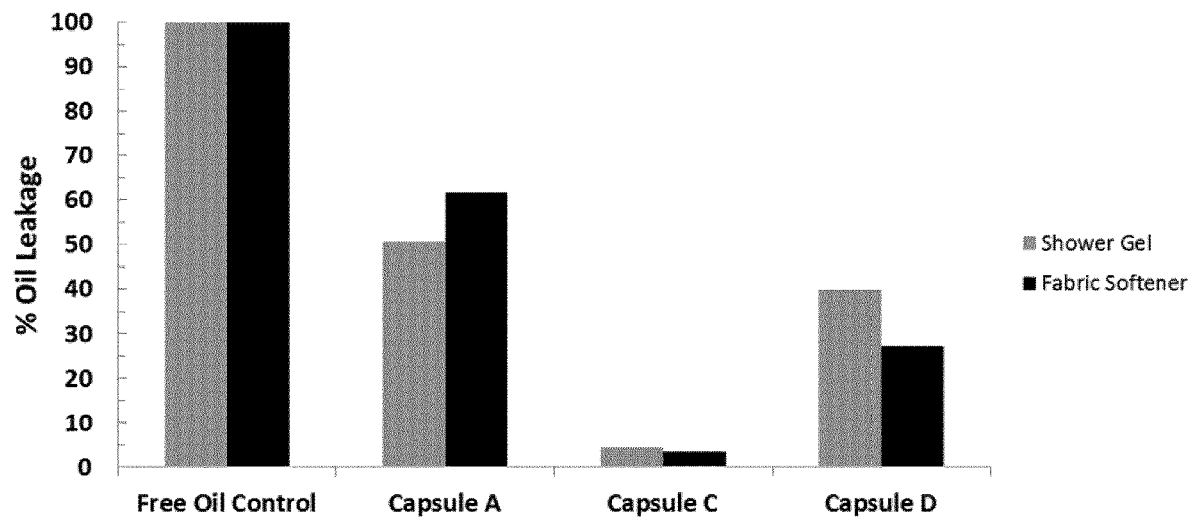
FIG. 9 represents the perfume oil leakage of microcapsules of the invention in fabric softener and shower gel bases (37° C.—1 week).

[1]Tetrasodium EDTA; origin: BASF
[2]Acrylates copolymer; origin: Noveon
[3]Sodium C12-C15 Pareth Sulfate; origin: Zschimmer & Schwarz
[4]Methylchloroisothiazolinone and methylisothiazolinone; origin: Rohm & Haas One can conclude from FIG. 9, that even with the limited amount of polyisocyanate, microcapsules of the invention exhibit significant encapsulation and stabilization of fragrance oil. The capsules retain significant oil after incubation in harsh and complex application formulations for 1 week at 37° C., which serves as an accelerated stability test indicative of longer term stability and performance. Stability results are plotted against the equivalent loading of free perfume oil in shower gel and fabric softener applications.

Example 6

Performance in AP/DEO Application

Figure 10:
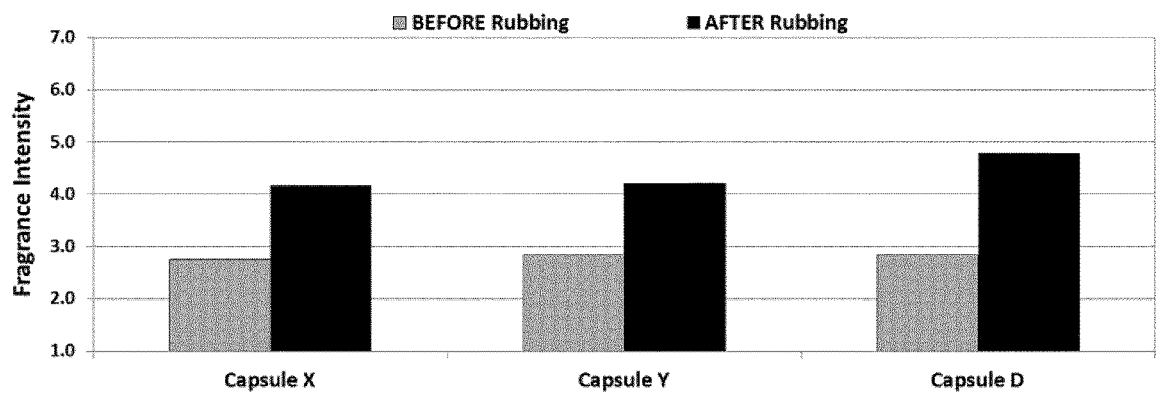
FIG. 10 represents olfactive impact of microcapsules slurries in antiperspirant base from blotters before and after rubbing.

Protocol for evaluating the olfactive impact of microcapsules before and after rubbing from an antiperspirant/deodorant application base is as follows. A 3 inch by 5 inch piece of blotter paper was dosed with 150 mg of a roll-on antiperspirant application base, with a composition according to that found in New Table 10, dosed with microcapsule slurry equivalent to 0.2 percent by weight fragrance oil overall. The base was gently and evenly spread over the blotter paper carefully so as not to remove any base, then allowed to dry over 24 hours at room temperature. The blotters were then evaluated as is by panelists (n=15) for sensory impact using a scale from 1 to 7 for olfactive intensity (1=no perceivable fragrance, to 7=extremely strong fragrance intensity). The fragrance intensity was then evaluated again using the same intensity scale after rubbing the surface of the blotter paper three times. The data illustrated in FIG. 10 shows the average olfactive intensity of each sample evaluated from the blotters before and after rubbing. The results of this scratch-and-sniff test from blotters demonstrate that there is a significant burst effect and sensory performance of capsules.

TABLE 10

Antiperspirant base composition

| Ingredient | Active Amount (% Wt) | Function |
|---|---|---|
| Steareth-2 | 3.25 | Emulsifier |
| Steareth-21 | 0.75 | Emulsifier |
| PPG-15 Stearyl Ether | 4 | Emollient |
| Deionized Water | 51.8 | Solvent |
| Aluminum Chlorohydrate (50% aqueous solution) | 40 | Antiperspirant |
| Microcapsule Slurry (Equivalent Oil) | 0.2 | Fragrance |

Example 7

Stability in a Surfactant Composition

Figure 11:
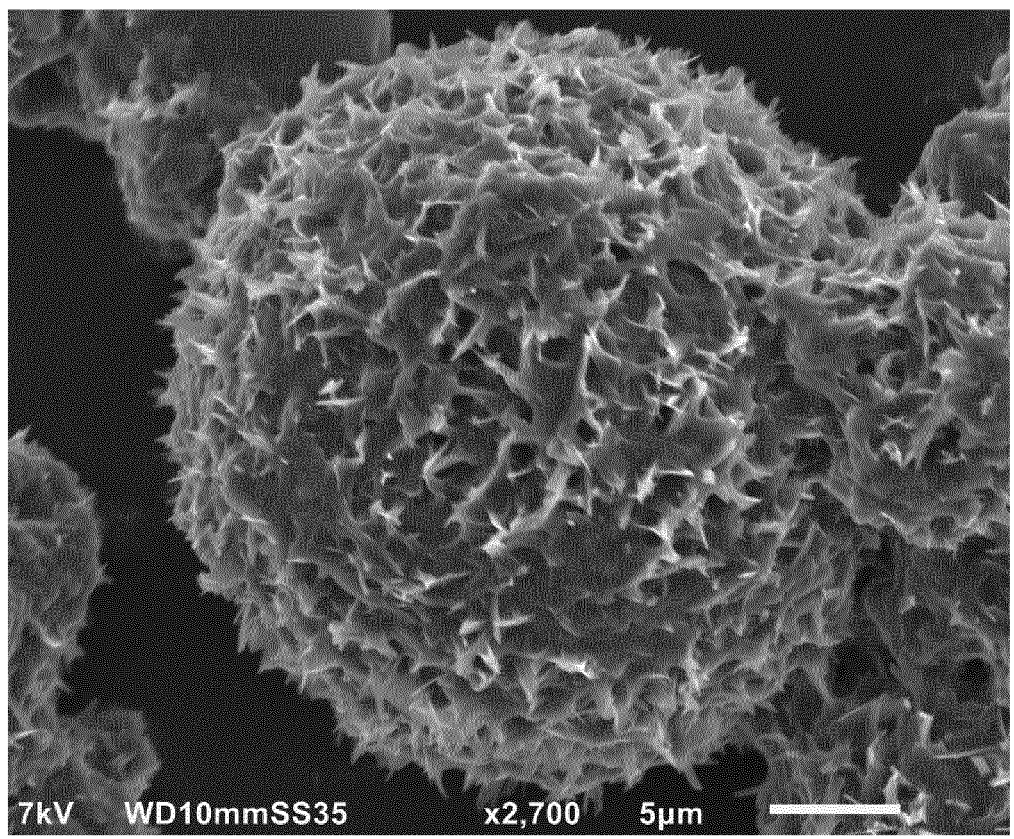
FIG. 11 represents scanning electron micrographs of mineralized microcapsules according to the invention (Capsules C) that have been incubated for three months in a model surfactant mixture.

FIG. 11 represents scanning electron micrographs of mineralized microcapsules according to the invention (Capsules C) that have been incubated for three months in the model surfactant mixture according to Table 7.

Example 8

Spray-Dried Microcapsules Preparation

Emulsions A-E having the following ingredients are prepared.

TABLE 11

Composition of Emulsions A-E and composition of granulated powder A-E after spray-drying

| Ingredients | Emulsion A | Emulsion B | Emulsion C | Emulsion D | Emulsion E |
|---|---|---|---|---|---|
| Modified starch [1] | 2.6% | 2.6% | 2.6% | 12.5% | 2% |
| Maltodextrin [2] | 26.8% | 22.8% | 19.3% | 0% | 19.1% |
| Maltose [3] | 0% | 0% | 0% | 7.9% | 0% |
| Citric Acid | 0% | 0% | 0% | 1% | 0% |
| Tripotassium Citrate | 0% | 0% | 0% | 1.9% | 0% |
| Microcapsules A-D | 12.0% | 24% | 37.0% | 8.9% | 56.2% |
| Silica [4] | 1.1% | 1.1% | 1.1% | 0% | 0% |
| Free Perfume B [5] | 0% | 0% | 0% | 11% | 0% |
| Water | 57.6% | 49.6% | 40.1% | 56.9% | 22.7% |

| | Granule A | Granule B | Granule C | Granule D | Granule E |
|---|---|---|---|---|---|
| Modified starch [1] | 7.5% | 7.4% | 7.2% | 31.6% | 4.9% |
| Maltodextrin [2] | 77.4% | 65.5% | 53.8% | 0% | 44.7% |
| Maltose | 0% | 0% | 0% | 20.9% | 0% |
| Citric Acid | 0% | 0% | 0% | 2.6% | 0% |
| Tripotassium citrate | 0% | 0% | 0% | 4.9% | 0% |
| Encapsulated perfume B | 0% | 0% | 0% | 28.1% | 0% |
| Microcapsules A-D | 12.% | 24.1% | 36.1% | 9.8% | 48.4% |
| Silica | 3.0 | 3.0% | 2.9% | 2.0% | 2% |
| Fragrance loading in powder after spray-drying | 10.1% | 20.1% | 30% | 35.8% | 40.2% |

[1] Capsul ™, Ingredion
[2] Maltodextrin 10DE origin: Roquette
[3] Maltose, Lehmann & Voss
[4] Silica, Evonik
[5] see table 12

TABLE 12

Composition of Perfume B

| Component | % |
|---|---|
| ACÉTATE DE 4-(1,1-DIMÉTHYLÉTHYL)-1-CYCLOHEXYLE [1] | 14.50 |
| LINALOL BJ | 10.50 |
| LILIAL ® [2] | 10.00 |
| ISO E SUPER [3] | 10.00 |
| CITRONELLYL NITRILE | 9.00 |
| DIPHENYLOXYDE | 6.50 |
| ISOBORNYL ACETATE | 6.00 |
| BETA IONONE | 6.00 |
| TRICYCLO[5.2.1.0~2,6~]DEC-3-EN-8-YL ACETATE (A) + TRICYCLO[5.2.1.0~2,6~]DEC-4-EN-8-YL ACETATE (B) [4] | 5.50 |
| ETHER MT | 4.00 |
| HEDIONE ® [5] | 4.00 |
| GERANIOL 60 | 3.00 |
| CITRAL | 2.50 |
| ALDEHYDE C 10 | 2.50 |
| ALLYL HEPTANOATE | 2.50 |
| ETHYL METHYL-2-BUTYRATE | 1.50 |

TABLE 12-continued

Composition of Perfume B

| Component | % |
|---|---|
| GERANYL ACETATE | 1.00 |
| 2,4-DIMETHYL-3-CYCLOHEXENE-1-CARBALDEHYDE [6] | 1.00 |

[1] Firmenich SA, Switzerland
[2] 3-(4-tert-butylphenyl)-2-methylpropanal, Givaudan SA, Vernier, Switzerland
[3] 1-(octahydro-2,3,8,8-tetramethyl-2-naphtalenyl)-1-ethanone, International Flavors & Fragrances, USA
[4] Firmenich SA, Switzerland
[5] Methyl dihydrojasmonate, Firmenich SA, Switzerland
[6] Firmenich SA, Switzerland Components for the polymeric matrix (Maltodextrin and Capsul™, or Capsul™, citric acid and tripotassium citrate) are added in water at 45-50° C. until complete dissolution.

For emulsion D, free perfume C is added to the aqueous phase.

Microcapsules slurry is added to the obtained mixture. Then, the resulting mixture is then mixed gently at 25° C. (room temperature).

Granulated powder A-E are prepared by spray-drying Emulsion A-E using a Sodeva Spray Dryer (Origin France), with an air inlet temperature set to 215° C. and a throughput set to 500 ml per hour. The air outlet temperature is of 105° C. The emulsion before atomization is at ambient temperature.

Example 9

Liquid Scent Booster Composition

A sufficient amount of microcapsule slurry A, B, C or D is weighed and mixed in a liquid scent booster (Table 13) to add the equivalent of 0.2% perfume.

TABLE 13

Liquid scent booster composition

| Ingredients | Amount (% wt) | | | | | |
|---|---|---|---|---|---|---|
| | 1 | 2 | 3 | 4 | 5 | 6 |
| Water | 71.20% | 89.5% | 78.8% | 79.4% | 70% | 70% |
| Propylene glycol | 20.30% | — | — | — | 20% | 20% |
| Polyethylene glycol ethers of decyl alcohol[1] | 4.00% | 6% | | | | |
| Polyethylene glycol ether of Lauryl Alcohol[2] | | | | | 4.00% | 4.00% |
| alkyl polyglucoside C8-C10[3] | | | 8.30% | 7.7% | | |
| Deceth-3[1] | 1.50% | | | | | |
| Lauryl lactate | | | | 1% | | |
| Lauric acid | | 1.5% | 1.60% | | | |
| Glyceryl Caprylate | | | | | 3.00% | 3.00% |
| Fragrance | 3.00% | 3.0% | 3.00% | 3.00% | 3.00% | 0% |

[1]Deceth-8; trademark and origin: KLK Oleo
[2]Laureth-9; ; trademark and origin
[3]Plantacare 2000UP; trademark and origin: BASF Different ringing gel compositions are prepared (compositions 1-6) according to the following protocol.

In a first step, the aqueous phase (water), the solvent (propylene glycol) if present and surfactants are mixed together at room temperature under agitation with magnetic stirrer at 300 rpm for 5 min.

In a second step, the linker is dissolved in the hydrophobic active ingredient (fragrance) at room temperature under agitation with magnetic stirrer at 300 rpm. The resulting mixture is mixed for 5 min.

Then, the aqueous phase and the oil phase are mixed together at room temperature for 5 min leading to the formation of a transparent or opalescent ringing gel.

Example 10

Liquid Detergent Composition

A sufficient amount of microcapsule slurry A, B, C or D is weighed and mixed in a liquid detergent (Table 14) to add the equivalent of 0.2% perfume.

TABLE 14

Liquid detergent composition

| Ingredients | Concentration [wt %] |
|---|---|
| Sodium $C_{14-17}$ Alkyl Sec Sulfonate[1] | 7 |
| Fatty acids, $C_{12-18}$ and $C_{18}$-unsaturated[2] | 7.5 |
| $C_{12/14}$ fatty alcohol polyglycol ether with 7 mol EO[3] | 17 |
| Triethanolamine | 7.5 |

TABLE 14-continued

Liquid detergent composition

| Ingredients | Concentration [wt %] |
|---|---|
| Propylene Glycol | 11 |
| Citric acid | 6.5 |
| Potassium Hydroxyde | 9.5 |
| Properase L[4] | 0.2 |
| Puradax EG L[4] | 0.2 |

TABLE 14-continued

Liquid detergent composition

| Ingredients | Concentration [wt %] |
|---|---|
| Purastar ST L[4] | 0.2 |
| Acrylates/Steareth-20 Methacrylate structuring Crosspolymer[5] | 6 |
| Deionized Water | 27.4 |

[1]Hostapur SAS 60; Origin: Clariant
[2]Edenor K 12-18; Origin: Cognis
[3]Genapol LA 070; Origin: Clariant
[4]Origin: Genencor International
[5]Aculyn 88; Origin: Dow Chemical

Example 11

Powder Detergent Composition

A sufficient amount of granules A-E is weighed and mixed in a powder detergent composition (Table 15) to add the equivalent of 0.2% perfume.

TABLE 15

Powder detergent composition

| Ingredients | Part |
|---|---|
| Anionic (Linear Alkyl Benzene Sulphonates) | 20% |
| Nonionics (Alcohol Ethoxylates (5-9 ethylene oxide) | 6% |

TABLE 15-continued

Powder detergent composition

| Ingredients | Part |
| --- | --- |
| Builders (zeolites, sodium carbonate) | 25% |
| Silicates | 6% |
| Sodium Sulphate | 35% |
| Others (Enzymes, Polymers, Bleach) | 7.5% |
| Spray-dried granule powder A-E | 0.5% |

Example 12

Concentrated all Purpose Cleaner Composition

A sufficient amount of microcapsule slurry A, B, C or D is weighed and mixed in a concentrated all-purpose cleaner composition (Table 16) to add the equivalent of 0.2% perfume.

TABLE 16 concentrated all-purpose cleaner composition

| Ingredients | Amount (% wt) | Function |
| --- | --- | --- |
| Ethoxylated Alcohol (C9-C11, 8EO) [1] | 20 | Non-ionic surfactant |
| Sodium Dodecyl Benzene Sulfonate [2] | 16 | Anionic surfactant |
| Sodium Cumene Sulfonate [3] | 8 | Hydrotrope |
| Methyl chloro isothiazolinone Methyl isothiazolinone 3.3:1 [4] | 0.8% | preservative |
| Water | 55.9 | solvent |

[1] Neodol 91-8 ®; trademark and origin: Shell Chemical
[2] Biosoft D-40 ®; trademark and origin: Stepan Company
[3] Stepanate SCS ®; trademark and origin: Stepan Company
[4] Kathon CG ®; trademark and origin: Dow Chemical Company All ingredients are mixed together and then the mixture was diluted with water to 100%.

Example 13

Solid Scent Booster Composition

The following compositions are prepared.

TABLE 17

Salt-based solid scent booster compositions

| Ingredients | Part |
| --- | --- |
| Sodium chloride | 95 |
| Spray-dried granule powder A-E | 5 |

TABLE 18

Urea-based solid scent booster compositions

| Ingredients | Part |
| --- | --- |
| Urea (beads) | 94 |
| Spray-dried granule powder A-E | 8 |
| Bentonite | 3 |
| Perfume | 3 |

Example 14

Shampoo Composition

A sufficient amount of microcapsule slurry A, B, C or D is weighed and mixed in a shampoo composition (Table 19) to add the equivalent of 0.2% perfume.

TABLE 19

Shampoo composition

| | Ingredients | Concentration [wt %] |
| --- | --- | --- |
| A | Water deionized | 44.4 |
| | Polyquaternium-10 [1] | 0.3 |
| | Glycerin 85% [2] | 1 |
| | DMDM Hydantoin [3] | 0.2 |
| B | Sodium Laureth Sulfate [4] | 28 |
| | Cocamidopropyl Betaine [5] | 3.2 |
| | Disodium Cocoamphodiacetate [6] | 4 |
| | Ethoxy (20) Stearyl Alcohol [6] | 1 |
| C | Sodium Laureth Sulfate [4] | 3 |
| | Glyceryl Laureate [7] | 0.2 |
| D | Water deionized | 1 |
| | Sodium Methylparaben [8] | 0.1 |
| E | Sodium Chloride 10% aqueous sol. | 15 |
| | Citric acid 10% aqueous sol. till pH 5.5-6 | q.s. |
| | Perfume | 0.5 |
| | TOTAL: | 100 |

[1] Ucare Polymer JR-400, Noveon
[2] Schweizerhall
[3] Glydant, Lonza
[4] Texapon NSO IS, Cognis
[5] Tego Betain F 50, Evonik
[6] Amphotensid GB 2009, Zschimmer & Schwarz
[7] Monomuls 90 L-12, Gruenau
[8] Nipagin Monosodium, NIPA Polyquaternium-10 is dispersed in water. The remaining ingredients of phase A are mixed separately by addition of one after the other while mixing well after each adjunction. Then this pre-mix is added to the Polyquaternium-10 dispersion and was mixed for 5 min. Then Phase B and the premixed Phase C (heat to melt Monomuls 90L-12 in Texapon NSO IS) are added. The mixture is mixed well. Then, Phase D and Phase E are added while agitating. The pH is adjusted with citric acid solution till pH: 5.5-6.0.

Example 15

Shampoo Composition

A sufficient amount of microcapsule slurry A, B, C or D is weighed and mixed in a shampoo composition (Table 20) to add the equivalent of 0.2% perfume.

TABLE 20

Shampoo composition

| | Ingredients | Concentration [wt %] |
| --- | --- | --- |
| A | Water deionized | 45.97 |
| | Tetrasodium EDTA [1] | 0.05 |
| | Guar Hydroxypropyltrimonium Chloride [2] | 0.05 |
| | Polyquaternium-10 [3] | 0.075 |
| B | NaOH 10% aqueous sol. | 0.3 |
| C | Ammonium Lauryl Sulfate [4] | 34 |
| | Ammonium Laureth Sulfate [5] | 9.25 |
| | Cocamidopropyl Betaine [6] | 2 |

TABLE 20-continued

Shampoo composition

| | Ingredients | Concentration [wt %] |
|---|---|---|
| | Dimethicone (&) C12-13 Pareth-4 (&) C12-13 Pareth-23 (&) Salicylic Acid [7] | 2.5 |
| D | Cetyl Alcohol [8] | 1.2 |
| | Cocamide MEA [9] | 1.5 |
| | Glycol Distearate [10] | 2 |
| E | Methylchloroisothiazolinone & Methylisothiazolinone [11] | 0 |
| | D-Panthenol 75% [12] | 0.1 |
| | Water deionized | 0.3 |
| F | Sodium Chloride 25% aqueous sol. | 0.6 |
| | TOTAL: | 100 |

[1] EDETA B Powder, BASF
[2] Jaguar C14 S, Rhodia
[3] Ucare Polymer JR-400, Noveon
[4] Sulfetal LA B-E, Zschimmer & Schwarz
[5] Zetesol LA, Zschimmer & Schwarz
[6] Tego Betain F 50, Evonik
[7] Xiameter MEM-1691, Dow Corning
[8] Lanette 16, BASF
[9] Comperlan 100, Cognis
[10] Cutina AGS, Cognis
[11] Kathon CG, Rohm & Haas
[12] D-Panthenol, Roche A premix comprising Guar Hydroxypropyltrimonium Chloride and Polyquaternium-10 are added to water and Tetrasodium EDTA while mixing. When the mixture is homogeneous, NaOH is added. Then, Phase C ingredients are added and the mixture was heat to 75° C. Phase D ingredients are added and mixed till homogeneous. The heating is stopped and temperature of the mixture is decreased to RT. At 45° C., ingredients of Phase E while mixing final viscosity is adjusted with 25% NaCl solution and pH of 5.5-6 is adjusted with 10% NaOH solution.

Example 16

Rinse-Off Hair Composition

A sufficient amount of microcapsule slurry A, B, C or D is weighed and mixed in a rinse-off composition (Table 21) to add the equivalent of 0.2% perfume.

TABLE 21 rinse-off composition

| | Ingredients | Concentration [wt %] |
|---|---|---|
| A | Water deionized | 81.8 |
| | Behentrimonium Chloride [1] | 2.5 |
| | Hydroxyethylcellulose [2] | 1.5 |
| B | Cetearyl Alcohol [3] | 4 |
| | Glyceryl Stearate (and) PEG-100 Stearate [4] | 2 |
| | Behentrimonium Methosulfate (and) Cetyl alcohol (and) Butylene Glycol [5] | 4 |
| | Ethoxy (20) Stearyl Alcohol [6] | 1 |
| C | Amodimethicone (and) Trideceth-12 (and) Cetrimonium Chloride [7] | 3 |

TABLE 21-continued rinse-off composition

| | Ingredients | Concentration [wt %] |
|---|---|---|
| | Chlorhexidine Digluconate [8] 20% aqueous solution | 0.2 |
| D | Citric acid 10% aqueous sol. till pH 3.5-4 | q.s. |
| | TOTAL: | 100 |

[1] Genamin KDMP, Clariant
[2] Tylose H10 Y G4, Shin Etsu
[3] Lanette O, BASF
[4] Arlacel 165, Croda
[5] Incroquat Behenyl TMS-50-PA-(MH), Croda
[6] Brij S20, Croda
[7] Xiameter MEM-949, Dow Corning
[8] Alfa Aesar Ingredients of Phase A are mixed until an uniform mixture was obtained. Tylose is allowed to completely dissolve. Then the mixture is heated up to 70-75° C. Ingredients of Phase B are combined and melted at 70-75° C. Then ingredients of Phase B are added to Phase A with good agitation and the mixing is continued until cooled down to 60° C. Then, ingredients of Phase C are added while agitating and keeping mixing until the mixture cooled down to 40° C. The pH is adjusted with citric acid solution till pH: 3.5-4.0.

Example 17

Antiperspirant Spray Anhydrous Composition

A sufficient amount of microcapsule slurry A, B, C or D is weighed and mixed in an antiperspirant spray anhydrous composition (Table 22) to add the equivalent of 0.2% perfume.

TABLE 22 antiperspirant spray anhydrous composition

| Ingredient | Amount (wt %) |
|---|---|
| Cyclomethicone[1] | 53.51 |
| Isopropyl miristate | 9.04 |
| Silica[2] | 1.03 |
| Quaternium-18-Hectorite[3] | 3.36 |
| Aluminium Chlorohydrate[4] | 33.06 |

[1] Dow Corning ® 345 Fluid; trademark and origin: Dow Corning
[2] Aerosil ®; trademark and origin: Evonik
[3] Bentone ® 38; trademark and origin: Elementis Specialities
[4] Micro Dry Ultrafine; origin: Reheis Using a high speed stirrer, Silica and Quaternium-18-Hectorite are added to the Isopropyl miristate and Cyclomethicone mixture. Once completely swollen, Aluminium Chlorohydrate is added portion wise under stirring until the mixture was homogeneous and without lumps. The aerosol cans are filled with 25% Suspension of the suspension and 75% of Propane/Butane (2,5 bar).

Example 18

Antiperspirant Spray Emulsion Composition

A sufficient amount of microcapsule slurry A, B, C or D is weighed and mixed in antiperspirant spray emulsion composition (Table 23) to add the equivalent of 0.2% perfume.

TABLE 23 antiperspirant spray emulsion composition

| Ingredient | Amount (wt %) |
|---|---|
| Polysorbate 65[1] (Part A) | 0.95 |
| Polyglyceryl-2 dipolyhydroxystearate[2] (Part A) | 1.05 |
| Cetyl PEG/PPG-10/1 Dimethicone[3] (Part A) | 2.75 |
| Cyclomethicone[4] (Part A) | 16.4 |
| Isopropylisostearate[5] (Part A) | 4.5 |
| Phenoxyethanol[6] (Part A) | 0.5 |
| Ethylhexylglycerin[7] (Part A) | 0.2 |
| C12-15 Alkyl Benzoate[8] (Part A) | 5.65 |
| Silica Silylate[9] (Part A) | 0.1 |
| Sodium Methylparaben[10] (Part B) | 0.1 |
| Aluminium Chlorohydrate[11] (Part B) | 20 |
| Water (Part B) | 44.47 |
| Fragrance (Part C) | 3.33 |

[1] Tween 65 trademark and origin: CRODA
[2] Dehymuls PGPH; trademark and origin: BASF
[3] Abil EM-90; trademark and origin: BASF
[4] Dow Corning 345 fluid; trademark and origin: Dow Corning
[5] Crodamol ipis; trademark and origin: CRODA
[6] Phenoxyethanol; trademark and origin: LANXESS
[7] Sensiva sc 50; trademark and origin: KRAFT
[8] Tegosoft TN; trademark and origin: Evonik
[9] Aerosil R 812; trademark and origin: Evonik
[10] Nipagin mna; trademark and origin: CLARIANT
[11] Locron L; trademark and origin: CLARIANT The ingredients of Part A and Part B are weighted separately. Ingredients of Part A are heated up to 60° C. and ingredients of Part B are heated to 55° C. Ingredients of Part B are poured small parts while continuous stirring into A. Mixture were stirred well until the room temperature was reached. Then, ingredients of part C are added. The emulsion is mixed and is introduced into the aerosol cans. The propellant is crimped and added.

Aerosol filling: 30% Emulsion: 70% Propane/Butane 2,5 bar

Example 19

Deodorant Spray Composition

A sufficient amount of microcapsule slurry A, B, C or D is weighed and mixed in antiperspirant deodorant spray composition (Table 24) to add the equivalent of 0.2% perfume.

TABLE 24 deodorant spray composition

| Ingredient | Amount (wt %) |
|---|---|
| Ethanol 95% | 90.65 |
| Triclosan[1] | 0.26 |
| Isopropyl miristate | 9.09 |

[1] Irgasan ® DP 300; trademark and origin: BASF

All the ingredients according to the sequence of the Table 24 are mixed and dissolved. Then the aerosol cans are filled, crimp and the propellant is added (Aerosol filling: 40% active solution 60% Propane/Butane 2.5 bar).

Example 20

Antiperspirant Roll-on Emulsion Composition

A sufficient amount of microcapsule slurry A, B, C or D is weighed and mixed in antiperspirant roll-on emulsion composition (Table 25) to add the equivalent of 0.2% perfume.

TABLE 25 antiperspirant roll-on emulsion composition

| Ingredient | Amount (wt %) |
|---|---|
| Steareth-2[1] (Part A) | 3.25 |
| Steareth-21[2] (Part A) | 0.75 |
| PPG-15 Stearyl Ether[3] (Part A) | 4 |
| WATER deionised (Part B) | 51 |
| Aluminum Chlorohydrate 50% aqueous solution[4] (Part C) | 40 |
| Fragrance (Part D) | 1 |

[1] BRIJ 72; origin: ICI
[2] BRIJ 721; origin: ICI
[3] ARLAMOL E; origin: UNIQEMA-CRODA
[4] LOCRON L; origin: CLARIAN Part A and B are heated separately to 75° C.; Part A is added to part B under stirring and the mixture is homogenized for 10 minutes. Then, the mixture is cooled down under stirring; and part C is slowly added when the mixture reached 45° C. and part D when the mixture reached at 35° C. while stirring. Then the mixture is cooled down to RT.

Example 21

Antiperspirant Roll-on Composition

A sufficient amount of microcapsule slurry A, B, C or D is weighed and mixed in antiperspirant roll-on composition (Table 26) to add the equivalent of 0.2% perfume.

TABLE 26 antiperspirant roll-on composition

| Ingredient | QUANTITY |
|---|---|
| Water (Part A) | 45 |
| Aluminum Chlorohydrate 50% aqueous solution[1] (Part B) | 20 |
| Alcohol Denat. (Ethanol 96%) (Part B) | 30 |
| Ceteareth-12[2] (Part C) | 2 |
| Ceteareth-30[3] (Part C) | 2 |
| Fragrance (Part D) | 1 |

[1] LOCRON L; origin: CLARIANT
[2] EUMULGIN B-1; origin: BASF
[3] EUMULGIN B-3; origin: BASF The ingredients of part B are mixed in the vessel then ingredient of part A is added. Then dissolved part C in part A and B. With perfume, 1 part of Cremophor RH40 for 1 part of perfume is added while mixing well

Example 22

Antiperspirant Roll-on Composition

A sufficient amount of microcapsule slurry A, B, C or D is weighed and mixed in antiperspirant roll-on emulsion composition (Table 27) to add the equivalent of 0.2% perfume.

TABLE 27 antiperspirant roll-on emulsion composition

| Ingredient | Amount (wt %) |
| --- | --- |
| Water (Part A) | 50.51 |
| Hydroxyethylcellulose[1] (Part A) | 0.71 |
| Ethanol 95 % (Part B) | 40.40 |
| 1,2-Propylene Glycol (Part B) | 5.05 |
| Triclosan[2] (Part B) | 0.30 |
| PEG-40 Hydrogenated castor oil[3] (Part C) | 3.03 |

[1] Natrosol® 250 H; trademark and origin: Ashland
[2] Irgasan® DP 300; trademark and origin: BASF
[3] Cremophor® RH 40; trademark and origin: BASF Part A is prepared by sprinkling little by little the Hydroxyethylcellulose in the water whilst rapidly stirring with the turbine. Stirring is continued until the Hydroxyethylcellulose is entirely swollen and giving a limpid gel. Then, Part B is poured little by little in Part A whilst continuing stirring until the whole is homogeneous. Part C is added.

Example 23

Deodorant Pump without Alcohol Formulation

A sufficient amount of microcapsule slurry A, B, C or D is weighed and mixed in the following composition (Table 28) to add the equivalent of 0.2% perfume.

TABLE 28 deodorant composition

| Ingredients | Amount (wt %) |
| --- | --- |
| C12-15 Alkyl Lactate[1] | 5 |
| Dimethicone[2] | 91.6 |
| Cetyl Lactate[3] | 1 |
| Octyl dodecanol[4] | 0.8 |
| Triclosan[5] | 0.1 |
| PERFUME | 1.5 |

[1] Ceraphyl 41; trademark and origin ASHLAND
[2] DOW CORNING 200 FLUID 0.65 cs; trademark and origin DOW CORNING CORPORATION
[3] Ceraphyl 28; trademark and origin ASHLAND
[4] Eutanol G; trademark and origin BASF
[5] Irgasan® DP 300; trademark and origin: BASF All the ingredients of Table 27 are mixed according to the sequence of the table and the mixture is heated slightly to dissolve the Cetyl Lactate.

Example 24

Deodorant Pump with Alcohol Formulation

A sufficient amount of microcapsule slurry A, B, C or D is weighed and mixed in the following composition (Table 29) to add the equivalent of 0.2% perfume.

TABLE 29 deodorant composition

| Ingredients | Amount (wt %) |
| --- | --- |
| Ethyl Alcohol (Part A) | 60 |
| PEG-6 Caprylic/Capric Glycerides[1] (Part A) | 2 |

TABLE 29-continued deodorant composition

| Ingredients | Amount (wt %) |
| --- | --- |
| Water (Part A) | 35.6 |
| PEG-40 Hydrogenated Castor Oil[2] (Part B) | 0.4 |
| PERFUME (Part B) | 2 |

[1] Softigen 767; trademark and origin CRODA
[2] Cremophor® RH 40; trademark and origin: BASF Ingredients from Part B are mixed together. Ingredients of Part A are dissolved according to the sequence of the Table and are poured into part B.

Example 25

Deodorant Stick without Alcohol Formulation

A sufficient amount of microcapsule slurry A, B, C or D is weighed and mixed in the following composition (Table 30) to add the equivalent of 0.2% perfume.

TABLE 30 deodorant composition

| Ingredient | Amount (wt %) |
| --- | --- |
| Stearic acid (Part A) | 5.05 |
| 1,2-propylene glycol (Part A) | 41.87 |
| Sodium hydroxide 20% aqueous solution (Part A) | 4.24 |
| Water (Part A) | 30.30 |
| Tetrasodium EDTA[1] (Part A) | 0.10 |
| Ceteareth-25[2] (Part A) | 1.52 |
| PPG-3 Myristyl ether[3] (Part A) | 1.52 |
| 1,2-propylene glycol (Part B) | 15.14 |
| Triclosan[4] (Part B) | 0.25 |

[1] Edeta® B Power; trademark and origin: BASF
[2] Cremophor® A25; trademark and origin: BASF
[3] Tegosoft® APM; trademark and origin: Evonik
[4] Irgasan® DP 300; trademark and origin: BASF All the components of Part A are weighted and heated up to 70-75° C. Ceteareth-25 is added once the other Part A ingredients are mixed and heated. Once the Ceteareth-25 is dissolved, the Stearic Acid is added. Part B is prepared by dissolving the Triclosan in 1,2 Propylene Glycol. Water which has evaporated is added. Slowly under mixing, Part B is poured into part A. To stock, a plastic bag into the bucket is put in to be sealed after cooling. Moulds was filled at about 70° C.

Example 26

Anti-Perspirant Stick

A sufficient amount of microcapsule slurry A, B, C or D is weighed and mixed in the following composition (Table 31) to add the equivalent of 0.2% perfume.

TABLE 31 deodorant composition

| Ingredient | Amount (wt %) |
| --- | --- |
| Cyclomethicone[1] (Part A) | 55.56 |
| Stearyl Alcohol[2] (Part A) | 21.21 |
| PPG-14 Butyl ether[3] (Part A) | 2.02 |
| Hydrogenated Castor Oil[4] (Part A) | 1.01 |
| Aluminium Zirconiumtetrachlorohydrex-Gly[5] (Part B) | 20.20 |

[1] Dow Corning® 345 Fluid; trademark and origin: Dow Corning
[2] Lanette® 18; trademark and origin: BASF
[3] Tegosoft® PBE; trademark and origin: Evonik
4) Cutina® HR; trademark and origin: BASF
[5] Summit AZP-908; trademark and origin: Reheis All the components of Part A are weighted, heated up to 70-75° C. and mixed well. Ingredient of Part B is dispersed in Part A. The mixture is mixed and putted into a tick at 65° C.

Example 27

Day Cream

A sufficient amount of microcapsule slurry A, B, C or D is weighed and mixed in the following composition (Table 32) to add the equivalent of 0.2% perfume.

TABLE 32 day cream

| Ingredients | % |
| --- | --- |
| ARLATONE 985 | 5.000 |
| Ethoxylated Fatty Alcohol Ester | |
| CETYL ALCOHOL | 0.500 |
| TEFOSE 2561 | 4.000 |
| Ceteth-20 (and) Glyceryl Stearate (and) PEG-6 Stearate (and) Steareth-20 | |
| COSBIOL | 1.000 |
| Squalan | |
| MINERAL OIL 30-40 cp | 2.000 |
| Paraffin Oil | |
| PETROLEUM JELLY | 6.000 |
| Petrolatum | |
| WATER deionized | 75.850 |
| PROPYLENE GLYCOL | 5.000 |
| GLYDANT PLUS | 0.150 |
| DMDM Hydantoin (and) Iodopropynyl Butylcarbamate | |
| PNC 400 | 0.200 |
| Sodium Carbomer | |
| PERFUME | 0.300 |
| Total | 100.00 |

Example 28

Talc Formulation

A sufficient amount of granules A-E is weighed and mixed in introduced in a standard talc base: 100% talc, very slight characteristic odor, white powder, origin: LUZENAC to add the equivalent of 0.2% perfume.

Example 29

Shower-Gel Composition

A sufficient amount of microcapsule slurry A, B, C or D is weighed and mixed in the following composition (Table 33) to add the equivalent of 0.2% perfume.

TABLE 33 shower gel composition

| Ingredients | Amount (% wt) | Function |
| --- | --- | --- |
| WATER deionised | 49.350 | Solvent |
| Tetrasodium EDTA[1] | 0.050 | Chelating agent |
| Acrylates Copolymer[2] | 6.000 | Thickener |
| Sodium C12-C15 Pareth Sulfate[3] | 35.000 | Surfactant |
| Sodium Hydroxide 20% aqueous solution | 1.000 | pH adjuster |
| Cocamidopropyl Betaine[4] | 8.000 | Surfactant |
| Methylchloroisothiazolinone and Methylisothiazolinone[5] | 0.100 | Preservative |
| Citric Acid (40%) | 0.500 | pH adjuster |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS Ingredients are mixed, pH is adjusted to 6-6.3 (Viscosity: 4500 cPo+/−1500 cPo (Brookfield RV/Spindle #4/20 RPM)).

Example 30

Shower-Gel Composition

A sufficient amount of microcapsule slurry A, B, C or D is weighed and mixed in the following composition (Table 34) to add the equivalent of 0.2% perfume.

TABLE 34 shower gel composition

| Ingredients | Amount (% wt) | Function |
| --- | --- | --- |
| WATER deionized | 52.40 | Solvent |
| Tetrasodium EDTA[1] | 0.10 | Chelating agent |
| Sodium Benzoate | 0.50 | Preservative |
| Propylene Glycol | 2.00 | Solvent |
| Sodium C12-C15 Pareth Sulfate[2] | 35.00 | Surfactant |
| Cocamidopropyl Betaine[3] | 8.00 | Surfactant |
| Polyquaternium-7[4] | 0.20 | Conditioning agent |
| Citric Acid (40%) | 1.00 | pH adjuster |
| Sodium Chloride | 0.80 | Viscosity adjuster |

[1] EDETA B POWDER; trademark and origin: BASF
[2] ZETESOL AO 328 U; trademark and origin: ZSCHIMMER & SCHWARZ
[3] TEGO-BETAIN F 50; trademark and origin: GOLDSCHMIDT
[4] MERQUAT 550; trademark and origin: LUBRIZOL Ingredients are mixed, pH is adjusted to 4.5 (Viscosity: 3000 cPo+/−1500 cPo (Brookfield RV/Spindle #4/20 RPM)).

Example 31

Shower-Gel Composition

A sufficient amount of microcapsule slurry A, B, C or D is weighed and mixed in the following composition (Table 35) to add the equivalent of 0.2% perfume.

TABLE 35 shower gel composition

| Ingredients | Amount (% wt) | Function |
|---|---|---|
| WATER deionized | 50.950 | Solvent |
| Tetrasodium EDTA[1] | 0.050 | Chelating agent |
| Sodium Benzoate | 0.500 | Preservative |
| Glycerin 86% | 3.500 | Solvent |
| Sodium Laureth Sulfate[2] | 27.000 | Surfactant |
| Polyquaternium-7[3] | 1.000 | Conditioning Agent |
| Coco-Betaine[4] | 6.000 | Surfactant |
| PEG-120 Methyl Glucose trioleate[5] | 1.000 | Thickener |
| Citric Acid (40%) | 1.000 | pH adjuster |
| Glycol Distearate & Laureth-4 & Cocamidopropyl Betaine[6] | 3.000 | Pearlizing agent |
| Sodium Chloride 20% | 5.000 | Viscosity adjuster |
| PEG-40 Hydrogenated Castor Oil[7] | 1.000 | Viscosity adjuster |

[1]EDETA B POWDER; trademark and origin: BASF
[2]Texapon NSO IS; trademark and origin: COGNIS
[3]MERQUAT 550; trademark and origin: LUBRIZOL
[4]DEHYTON AB-30; trademark and origin: COGNIS
[5]GLUCAMATE LT; trademark and origin: LUBRIZOL
[6]EUPERLAN PK 3000 AM; trademark and origin: COGNIS
[7]CREMOPHOR RH 40; trademark and origin: BASF Ingredients are mixed, pH is adjusted to 4.5 (Viscosity: 4000 cPo+/−1500 cPo (Brookfield RV/Spindle #4/20 RPM))

Example 32

Hand Dishwash

A sufficient amount of microcapsule slurry A, B, C or D is weighed and mixed in the following composition (Table 36) to add the equivalent of 0.2% perfume.

TABLE 36

Hand dish wash composition

| Ingredients | Amount (% wt) | Function |
|---|---|---|
| Linear alkylbenzene sulfonic acid[1] | 20 | Anionic surfactant |
| Diethanolamide[2] | 3.5 | Foam booster |
| Sodium Hydroxide(50%)[3] | 3.4 | pH Adjuster/neutralizer |
| Secondary alcohol ethoxolate[4] | 2.5 | Non-ionic surfactant |
| Sodium xylene sulfonate | 6.3 | Hydrotrope |
| Water | 64.3 | Solvent |

[1]Biosoft S-118®; trademark and origin: Stepan Company
[2]Ninol 40-CO®; trademark and origin: Stepan Company
[3]Stepanate SXS®; trademark and origin: Stepan Company
[4]Tergitol 15-S-9®; trademark and origin: Dow Chemical Company Water with sodium hydroxide and diethanolamide are mixed. LAS is added. After the LAS is neutralized, the remaining ingredients are added. The pH was Checked (=7-8) and adjusted if necessary.

Example 33

Toothpaste Formulation

A sufficient amount of microcapsule slurry E (corresponding to microcapsules A except that a menthol flavor is encapsulated) is weighed and mixed in the following composition (Table 37) to add the equivalent of 0.2% flavor.

TABLE 37

Toothpaste formulation

| Ingredients | Amount (% wt) |
|---|---|
| Polyethylene glycol 400 | 2.0% |
| Xanthan Gum | 0.6% |
| Sorbitol 70% Solution | 50% |
| Sodium Fluoride | 0.220% |
| Sodium Benzoate | 0.2% |
| Water | 15.230% |
| Hydrated Silica[1] | 22.0% |
| Hydrated Silica[2] | 7.0% |
| Titanium Dioxide CI77891 | 0.5% |
| Sodium Lauryl Sulfate | 1.250% |
| Flavor | 1.2% |
| TOTAL | 100% |

[1]Tixosil 73; trademark and origin:
[2]Tixosil 43; trademark and origin:

Example 34

Dicalcium Phosphate Based Toothpaste Formulation

A sufficient amount of microcapsule slurry E (corresponding to microcapsules A except that a menthol flavor is encapsulated) is weighed and mixed in the following composition (Table 38) to add the equivalent of 0.2% flavor.

TABLE 38

Toothpaste formulation

| Ingredients | Amount (% wt) |
|---|---|
| Sodium carboxymethyl cellulose | 1.2% |
| Flavor | 1.2% |
| DI/Purified Water | Q.S to Final Wt. |
| Sodium Lauryl Sulfate | 1.3% |
| Glycerine | 20.0% |
| Sodium Saccharin | 0.2% |
| Dicalcium phosphate dihydrate | 36.0% |
| Methylparaben | 0.2% |
| Silica[1] | 3.0% |
| TOTAL | 100% |

[1]Aerosil®200; trademark and origin:

Example 35

Mouthwash Alcohol Free Formulation

A sufficient amount of microcapsule slurry E (corresponding to microcapsules A except that a menthol flavor is encapsulated) is weighed and mixed in the following composition (Table 39) to add the equivalent of 0.2% flavor.

TABLE 39

Mouthwash formulation

| Ingredients | Amount (% wt) |
|---|---|
| Propylene Glycol | 10% |
| Flavor | 0.240% |
| DI/Purified Water | Q.S to Final Wt. |
| Poloxamer 407 NF | 0.240% |

TABLE 39-continued

Mouthwash formulation

| Ingredients | Amount (% wt) |
|---|---|
| Sodium Lauryl Sulfate | 0.040% |
| Sorbitol 70% Solution | 10.0% |
| Sodium Saccharin | 0.030% |
| Glycerine | 3.0% |
| Sodium Benzoate | 0.100% |
| Sucralose | 0.020% |
| Benzoic Acid | 0.050% |
| TOTAL | 100% |

Example 36

Mouthwash Formulation

A sufficient amount of microcapsule slurry E (corresponding to microcapsules A except that a menthol flavor is encapsulated) is weighed and mixed in the following composition (Table 40) to add the equivalent of 0.2% flavor.

TABLE 40

Mouthwash formulation

| Ingredients | Amount (% wt) |
|---|---|
| Ethyl Alcohol 190 Proof | 15.0% |
| Flavor | 0.240% |
| DI/Purified Water | Q.S to Final Wt. |
| Poloxamer 407 NF | 0.240% |
| Sodium Lauryl Sulfate | 0.040% |
| Sorbitol 70% Solution | 10.0% |
| Sodium Saccharin | 0.030% |
| Glycerine | 3.0% |
| Sodium Benzoate | 0.100% |
| Sucralose | 0.020% |
| Benzoic Acid | 0.050% |
| TOTAL | 100% |

62/687,878, filed Jun. 21, 2018, and which claims the benefit of priority to European Patent Application No. 18184288.1, filed Jul. 18, 2018, the entire contents of which are hereby incorporated by reference herein.

The invention claimed is:

1. A process for preparing a mineralized core-shell microcapsule slurry comprising the steps of:
   (i) dissolving at least one polyisocyanate having at least two isocyanate groups in an oil comprising a hydrophobic material to form an oil phase;
   (ii) preparing an aqueous solution of a charged emulsifier to form a water phase;
   (iii) adding the oil phase to the water phase to form an oil-in-water emulsion;
   (iv) applying conditions suitable to induce interfacial polymerization to form core-shell microcapsules in the form of a slurry;
   (v) adsorption of at least one mineral precursor on the microcapsule shell; and
   (vi) applying conditions suitable to induce growth of a mineral layer on the microcapsule shell,
   wherein the polyisocyanate is added in an amount between 0.1% and 0.8% by weight based on the total weight of the slurry of step (iv).

2. The process according to claim 1, wherein the emulsifier is an anionic emulsifier and forms an anionic surface when the interfacial polymerization is completed in step (iv).

3. The process according to claim 2, wherein the emulsifier is selected from the group consisting of polyvinyl alcohol, polyvinyl pyrrolidone, gum acacia, casein, sodium caseinate, soy protein, hydrolyzed soy protein, pea protein, milk protein, whey protein, pectin, sugar beet pectin, sericin, bovine serum albumin, gelatin, and mixtures thereof.

4. The process according to claim 1, wherein the mineral precursor is adsorbed on the microcapsule shell by incubating the core-shell microcapsules in at least one mineral precursor solution, wherein the mineral precursor solution is selected from the group consisting of iron (II) sulfate solution, iron (III) chloride solution, calcium-based salt solution, phosphate-based salt solution, carbonate based salt solution, titanium-based precursor solution, zinc-based precursor solution, and mixtures thereof.

5. The process according to claim 1, wherein the mineral precursor does not comprise silicon oxides.

6. The process according to claim 1, wherein the mineral growth in step (vi) is induced by incubating the microcapsules obtained in step (v) in a second oppositely charged mineral precursor solution or in a solution to induce the mineralization of the mineral precursor of step (v).

7. The process according to claim 6, wherein the first mineral precursor solution is a calcium-based solution and the second mineral precursor solution is a phosphate-based solution or the first mineral precursor solution is a calcium-based solution and the second mineral precursor solution is a carbonate-based solution.

8. A mineralized core-shell microcapsule slurry comprising at least one microcapsule made of:
   an oil-based core;
   a polyurea shell or a polyurethane shell, and
   a mineral layer,
   wherein the polyurea or the polyurethane shell comprises between 0.1% and 0.8% by weight of a polyisocyanate having at least two isocyanate groups based on the total weight of the slurry.

9. The mineralized core-shell microcapsule slurry according to claim 8, wherein the mineral layer comprises a material selected from the group consisting of iron oxides, iron oxyhydroxide, titanium oxides, zinc oxides, calcium carbonates, calcium phosphates, and mixtures thereof.

10. A perfuming composition comprising
    (i) the mineralized core-shell microcapsule slurry according to claim 8, wherein the mineralized core-shell microcapsule slurry further comprises a hydrophobic material comprising a perfume,
    (ii) at least one ingredient selected from the group consisting of a perfumery carrier and a perfumery base; and
    (iii) optionally at least one perfumery adjuvant.

11. A consumer product comprising:
    a personal care active base, and
    the mineralized core-shell microcapsule slurry according to claim 8,
    wherein the consumer product is in the form of a personal care composition.

12. A consumer product comprising:
    a home care or a fabric care active base, and
    the mineralized core-shell microcapsule slurry according to claim 8,
    wherein the consumer product is in the form of a home care or a fabric care composition.

13. The process according to claim 1, wherein the hydrophobic material is a perfume oil.

14. The process according to claim 1, wherein the polyisocyanate is added in an amount between 0.3% and 0.8% by weight based on the total weight of the slurry of step (iv).

15. A consumer product comprising:
a personal care active base, and
the perfuming composition according to claim 10,
wherein the consumer product is in the form of a personal care composition.

16. The consumer product of claim 15, wherein the consumer product is in the form of a shampoo, a hair-conditioner or a shower gel.

17. A consumer product comprising:
a home care or a fabric care active base, and
the perfuming composition according to claim 10,
wherein the consumer product is in the form of a home care or a fabric care composition.

18. The consumer product of claim 17, wherein the consumer product is in the form of a detergent or a fabric softener.

* * * * *